US009168718B2

(12) United States Patent
Westwood et al.

(10) Patent No.: US 9,168,718 B2
(45) Date of Patent: Oct. 27, 2015

(54) METHOD FOR PRODUCING TEMPERATURE RESISTANT NONWOVENS

(75) Inventors: Alistair Duncan Westwood, Kingwood, TX (US); Michael Glenn Williams, Houston, TX (US); Galen Charles Richeson, Humble, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 408 days.

(21) Appl. No.: 12/723,317

(22) Filed: Mar. 12, 2010

(65) Prior Publication Data

US 2010/0267914 A1 Oct. 21, 2010

(51) Int. Cl.

| | |
|---|---|
| ***B32B 5/04*** | (2006.01) |
| ***B32B 5/26*** | (2006.01) |
| ***B32B 37/15*** | (2006.01) |
| ***D04H 3/007*** | (2012.01) |
| ***D04H 3/16*** | (2006.01) |

(Continued)

(52) U.S. Cl.

CPC ............... *B32B 5/02* (2013.01); *A61F 13/4902* (2013.01); *A61F 13/51464* (2013.01); *B32B 5/04* (2013.01); *B32B 5/26* (2013.01); *B32B 37/153* (2013.01); *D04H 1/42* (2013.01); *D04H 1/4291* (2013.01); *D04H 3/007* (2013.01); *D04H 3/16* (2013.01); *B32B 2250/20* (2013.01); *B32B 2262/0253* (2013.01); *B32B 2307/51* (2013.01); *B32B 2310/0887* (2013.01)

(58) Field of Classification Search

CPC . A61F 13/4902; A61F 13/51464; B32B 5/04; B32B 5/26; B32B 37/153; B32B 2250/20; B32B 2262/0253; B32B 2307/51; B32B 2310/0887; D04H 1/4291; D04H 3/14; D04H 3/16

USPC ........... 156/148, 167, 176, 181, 272.2, 275.5; 442/329

See application file for complete search history.

(56) References Cited

U.S. PATENT DOCUMENTS

| | | | |
|---|---|---|---|
| 3,149,178 | A | 9/1964 | Hamilton et al. |
| 3,338,992 | A | 8/1967 | Kinney |

(Continued)

FOREIGN PATENT DOCUMENTS

| | | | |
|---|---|---|---|
| CA | 1 268 753 | | 5/1990 |
| CN | 1962985 | A * | 5/2007 |

(Continued)

OTHER PUBLICATIONS

Dharmarajan, N. et al., *"Tailoring the Performance of Specialty Polyolefin Elastomer Based Elastic Nonwoven Fabrics"*, INTC® 2006, International Nonwovens Technical Conference, Conference Proceedings, Houston, TX, United States, Sep. 25-28, 2006.

(Continued)

*Primary Examiner* — Michael Tolin

(57) ABSTRACT

Temperature resistant multilayer composites, methods for making same, and articles made therefrom. The method can include extruding one or more polyolefin polymers having a MFR from less than 90 dg/min through at least one die having a plurality of nozzles to form a plurality of continuous fibers, at least one die operating at a melt pressure from greater than 500 psi (3447 kPa) to form at least one elastic meltblown layer; adhering the at least one elastic meltblown layer to at least one extensible layer to form a multilayer composite; and at least partially crosslinking the elastic meltblown layer or the extensible layer or both.

7 Claims, 5 Drawing Sheets

(51) Int. Cl.

| | |
|---|---|
| ***B32B 5/02*** | (2006.01) |
| ***A61F 13/49*** | (2006.01) |
| ***A61F 13/514*** | (2006.01) |
| ***D04H 1/42*** | (2012.01) |
| ***D04H 1/4291*** | (2012.01) |

(56) References Cited

U.S. PATENT DOCUMENTS 3,341,394 A 9/1967 Kinney
3,502,763 A 3/1970 Hartmann
3,542,615 A 11/1970 Dobo et al.
3,692,618 A 9/1972 Dorschner et al.
3,802,817 A 4/1974 Matsuki et al.
3,849,241 A 11/1974 Butin et al.
4,042,740 A 8/1977 Krueger
4,100,324 A 7/1978 Anderson et al.
4,103,058 A 7/1978 Humlicek
4,105,381 A 8/1978 Platt et al.
4,116,892 A 9/1978 Schwarz
4,144,008 A 3/1979 Schwarz
4,153,751 A 5/1979 Schwarz
4,177,312 A 12/1979 Rasen et al.
4,209,563 A 6/1980 Sisson
4,223,059 A 9/1980 Schwarz
4,251,585 A 2/1981 Schwarz
4,252,590 A 2/1981 Rasen et al.
4,285,100 A 8/1981 Schwarz
4,289,832 A 9/1981 Schwarz
4,340,563 A 7/1982 Appel et al.
4,368,565 A 1/1983 Schwarz
4,380,570 A 4/1983 Schwarz
4,410,602 A 10/1983 Komoda et al.
4,461,872 A 7/1984 Su
4,540,753 A 9/1985 Cozewith et al.
4,657,802 A 4/1987 Morman
4,775,579 A 10/1988 Hagy et al.
4,818,464 A 4/1989 Lau
4,827,064 A 5/1989 Wu
4,827,073 A 5/1989 Wu
4,939,016 A * 7/1990 Radwanski et al. .......... 428/152
4,950,720 A 8/1990 Randall, Jr. et al.
4,965,122 A 10/1990 Morman
4,981,747 A 1/1991 Morman
5,017,714 A 5/1991 Welborn, Jr.
5,055,438 A 10/1991 Canich
5,057,475 A 10/1991 Canich et al.
5,078,935 A 1/1992 Kobayashi et al.
5,096,867 A 3/1992 Canich
5,108,820 A 4/1992 Kaneko et al.
5,108,827 A 4/1992 Gessner
5,114,787 A 5/1992 Chaplin et al.
5,130,076 A 7/1992 Blatz et al.
5,143,679 A 9/1992 Weber et al.
5,145,727 A 9/1992 Potts et al.
5,147,712 A 9/1992 Miyahara et al.
5,153,157 A 10/1992 Hlatky et al.
5,156,793 A 10/1992 Buell et al.
5,160,746 A * 11/1992 Dodge et al. ...................... 425/7
5,167,897 A 12/1992 Weber et al.
5,171,908 A 12/1992 Rudnick
5,182,162 A 1/1993 Andrusko
5,187,005 A 2/1993 Stahle et al.
5,188,885 A 2/1993 Timmons et al.
5,190,812 A 3/1993 Joseph et al.
5,198,401 A 3/1993 Turner et al.
5,226,992 A 7/1993 Morman
5,227,224 A 7/1993 Ishikawa et al.
5,230,949 A 7/1993 Howard et al.
5,234,423 A 8/1993 Alemany et al.
5,238,733 A 8/1993 Joseph et al.
5,240,894 A 8/1993 Burkhardt et al.
5,242,436 A 9/1993 Weil et al.
5,244,724 A 9/1993 Antonacci et al.
5,260,126 A 11/1993 Collier, IV et al.
5,264,405 A 11/1993 Canich
5,272,003 A 12/1993 Peacock
5,288,791 A 2/1994 Collier, IV et al.
5,292,389 A 3/1994 Tsuji et al.
5,294,482 A 3/1994 Gessner
5,306,545 A 4/1994 Shirayanagi et al.
5,320,891 A 6/1994 Levy et al.
5,324,576 A 6/1994 Reed et al.
5,324,580 A 6/1994 Allan et al.
5,324,800 A 6/1994 Welborn, Jr. et al.
5,330,458 A 7/1994 Buell et al.
5,330,829 A 7/1994 Miller
5,332,613 A 7/1994 Taylor et al.
5,334,636 A 8/1994 Fujii et al.
5,336,457 A 8/1994 Wu et al.
5,336,545 A 8/1994 Morman
5,346,756 A 9/1994 Ogale et al.
5,349,016 A 9/1994 DeNicola, Jr. et al.
5,358,500 A 10/1994 Lavon et al.
5,366,782 A 11/1994 Curro et al.
5,366,786 A 11/1994 Connor et al.
5,366,793 A 11/1994 Fitts, Jr. et al.
5,368,584 A 11/1994 Clear et al.
5,368,919 A 11/1994 Robeson
5,368,927 A 11/1994 Lesca et al.
5,372,885 A 12/1994 Tabor et al.
5,382,400 A 1/1995 Pike et al.
5,382,461 A 1/1995 Wu
5,385,775 A 1/1995 Wright
5,393,599 A 2/1995 Quantrille et al.
5,418,045 A 5/1995 Pike et al.
5,422,172 A 6/1995 Wu
5,425,987 A 6/1995 Shawver et al.
5,455,110 A 10/1995 Connor
5,464,401 A 11/1995 Hasse et al.
5,466,411 A 11/1995 Butterfass et al.
5,472,775 A 12/1995 Obijeski et al.
5,476,616 A 12/1995 Schwarz
5,482,765 A 1/1996 Bradley et al.
5,482,772 A 1/1996 Strack et al.
5,492,753 A 2/1996 Levy et al.
5,496,298 A 3/1996 Kuepper et al.
5,507,475 A 4/1996 Seel et al.
5,507,736 A 4/1996 Clear et al.
5,523,141 A 6/1996 Fyler
5,534,339 A 7/1996 Stokes
5,534,340 A 7/1996 Gupta et al.
5,536,563 A 7/1996 Shah et al.
5,540,976 A 7/1996 Shawver et al.
5,549,964 A 8/1996 Shohji et al.
5,556,392 A 9/1996 Koczab
5,573,841 A 11/1996 Adam et al.
5,575,783 A 11/1996 Clear et al.
5,591,152 A 1/1997 Buell et al.
5,593,768 A 1/1997 Gessner
5,607,798 A 3/1997 Kobylivker et al.
5,616,408 A 4/1997 Oleszczuk et al.
5,620,785 A 4/1997 Watt et al.
5,628,741 A 5/1997 Buell et al.
5,635,290 A 6/1997 Stopper et al.
5,641,445 A 6/1997 Fauble et al.
5,643,662 A 7/1997 Yeo et al.
5,645,542 A 7/1997 Anjur et al.
5,645,933 A 7/1997 Sakazume et al.
5,652,051 A 7/1997 Shawver et al.
5,653,704 A 8/1997 Buell et al.
5,672,415 A 9/1997 Sawyer et al.
5,674,216 A 10/1997 Buell et al.
5,681,646 A 10/1997 Ofosu et al.
5,688,157 A 11/1997 Bradley et al.
5,690,627 A 11/1997 Clear et al.
5,695,849 A 12/1997 Shawver et al.
5,695,868 A 12/1997 McCormack
5,698,480 A 12/1997 Geiman et al.
5,720,832 A 2/1998 Minto et al.
5,723,217 A 3/1998 Stahl et al.
5,733,822 A 3/1998 Gessner et al.
5,783,531 A 7/1998 Andrew et al.
5,804,286 A 9/1998 Quantrille et al.
5,817,403 A 10/1998 Gillyns et al.

(56) References Cited

U.S. PATENT DOCUMENTS

| | | | |
|---|---|---|---|
| 5,824,613 | A | 10/1998 | Geiman et al. |
| 5,840,412 | A | 11/1998 | Wood et al. |
| 5,843,057 | A | 12/1998 | McCormack |
| 5,843,068 | A | 12/1998 | Allen et al. |
| 5,861,202 | A | 1/1999 | Kimura et al. |
| 5,866,488 | A | 2/1999 | Terada et al. |
| 5,874,160 | A | 2/1999 | Keck |
| 5,880,241 | A | 3/1999 | Brookhart et al. |
| 5,883,028 | A | 3/1999 | Morman et al. |
| 5,906,879 | A | 5/1999 | Huntoon et al. |
| 5,910,362 | A | 6/1999 | Aratake et al. |
| 5,914,084 | A | 6/1999 | Benson et al. |
| 5,914,184 | A | 6/1999 | Morman |
| 5,916,207 | A | 6/1999 | Toyoda et al. |
| 5,921,973 | A | 7/1999 | Newkirk et al. |
| 5,928,740 | A | 7/1999 | Wilhoit et al. |
| 5,942,451 | A | 8/1999 | Daponte et al. |
| 5,945,215 | A | 8/1999 | Bersted et al. |
| 5,952,252 | A | 9/1999 | Shawver et al. |
| 5,985,193 | A | 11/1999 | Harrington et al. |
| 5,993,714 | A | 11/1999 | Sawyer et al. |
| 5,994,244 | A | 11/1999 | Fujiwara et al. |
| 6,015,605 | A | 1/2000 | Tsujiyama et al. |
| 6,015,617 | A | 1/2000 | Maugans et al. |
| 6,015,764 | A | 1/2000 | McCormack et al. |
| 6,028,240 | A | 2/2000 | Wessel et al. |
| 6,037,281 | A | 3/2000 | Mathis et al. |
| 6,045,898 | A | 4/2000 | Kishi et al. |
| 6,071,451 | A | 6/2000 | Wang et al. |
| 6,075,179 | A | 6/2000 | McCormack et al. |
| 6,080,818 | A | 6/2000 | Thakker et al. |
| 6,083,583 | A | 7/2000 | Klocek et al. |
| 6,090,472 | A | 7/2000 | Wang et al. |
| 6,090,730 | A | 7/2000 | Fujiwara et al. |
| 6,096,668 | A | 8/2000 | Abuto et al. |
| 6,103,647 | A | 8/2000 | Shultz et al. |
| 6,114,261 | A | 9/2000 | Strelow et al. |
| 6,114,263 | A | 9/2000 | Benson et al. |
| 6,117,546 | A | 9/2000 | Geiman et al. |
| 6,140,551 | A | 10/2000 | Niemeyer et al. |
| 6,207,237 | B1 | 3/2001 | Haffner |
| 6,207,601 | B1 | 3/2001 | Maurer et al. |
| 6,207,602 | B1 | 3/2001 | Gessner et al. |
| 6,224,977 | B1 | 5/2001 | Kobylivker et al. |
| 6,261,674 | B1 | 7/2001 | Branham et al. |
| 6,268,203 | B1 | 7/2001 | Johnson et al. |
| 6,268,302 | B1 | 7/2001 | Ofosu et al. |
| 6,281,289 | B1 | 8/2001 | Maugans et al. |
| 6,286,145 | B1 | 9/2001 | Welchel et al. |
| 6,312,641 | B1 | 11/2001 | Hutchinson |
| 6,323,389 | B1 | 11/2001 | Thomas et al. |
| 6,342,565 | B1 | 1/2002 | Cheng et al. |
| 6,352,426 | B1 | 3/2002 | Hutchinson et al. |
| 6,355,348 | B1 | 3/2002 | Takesue et al. |
| 6,362,389 | B1 | 3/2002 | McDowall et al. |
| 6,372,172 | B1 | 4/2002 | Sudduth et al. |
| 6,391,408 | B1 | 5/2002 | Hutchinson |
| 6,410,465 | B1 | 6/2002 | Lim et al. |
| 6,417,121 | B1 | 7/2002 | Newkirk et al. |
| 6,417,122 | B1 | 7/2002 | Newkirk et al. |
| 6,420,285 | B1 | 7/2002 | Newkirk et al. |
| 6,443,940 | B1 | 9/2002 | Ashton et al. |
| 6,444,774 | B1 | 9/2002 | Stahl et al. |
| 6,458,726 | B1 | 10/2002 | Harrington et al. |
| 6,465,073 | B1 | 10/2002 | Morman et al. |
| 6,465,378 | B2 | 10/2002 | Gessner et al. |
| 6,476,289 | B1 | 11/2002 | Buell et al. |
| 6,478,785 | B1 | 11/2002 | Ashton et al. |
| 6,482,896 | B2 | 11/2002 | Maugans et al. |
| 6,503,853 | B1 | 1/2003 | Kassner et al. |
| 6,506,695 | B2 | 1/2003 | Gardner et al. |
| 6,506,698 | B1 | 1/2003 | Quantrille et al. |
| 6,516,472 | B2 | 2/2003 | Gessner et al. |
| 6,525,157 | B2 | 2/2003 | Cozewith et al. |
| 6,559,262 | B1 | 5/2003 | Waymouth et al. |
| 6,569,945 | B2 | 5/2003 | Bugada et al. |
| 6,572,598 | B1 | 6/2003 | Ashton et al. |
| 6,579,274 | B1 | 6/2003 | Morman et al. |
| 6,582,414 | B1 | 6/2003 | Richardson |
| 6,586,354 | B1 | 7/2003 | Topolkaraev et al. |
| 6,589,892 | B1 | 7/2003 | Smith et al. |
| 6,610,039 | B1 | 8/2003 | Wilhelm et al. |
| 6,627,564 | B1 | 9/2003 | Morman et al. |
| 6,632,212 | B1 | 10/2003 | Morman et al. |
| 6,649,546 | B2 | 11/2003 | Ohata |
| 6,649,547 | B1 | 11/2003 | Arnold et al. |
| 6,676,883 | B2 | 1/2004 | Hutchinson et al. |
| 6,717,028 | B1 | 4/2004 | Oberstadt |
| 6,723,669 | B1 * | 4/2004 | Clark et al. .................. 442/347 |
| 6,777,082 | B2 | 8/2004 | Patel et al. |
| 6,780,272 | B2 | 8/2004 | Wood |
| 6,881,793 | B2 | 4/2005 | Sheldon et al. |
| 6,881,800 | B2 | 4/2005 | Friedersdorf |
| 6,887,941 | B2 | 5/2005 | Zhou |
| 6,902,796 | B2 | 6/2005 | Morell et al. |
| 6,906,160 | B2 | 6/2005 | Stevens et al. |
| 6,909,028 | B1 | 6/2005 | Shawver et al. |
| 6,914,018 | B1 | 7/2005 | Uitenbroek et al. |
| 6,927,184 | B1 | 8/2005 | Jacobs-Hartwig et al. |
| 6,939,591 | B2 | 9/2005 | Hutchinson et al. |
| 6,946,413 | B2 | 9/2005 | Lange et al. |
| 6,960,635 | B2 | 11/2005 | Stevens et al. |
| 6,982,231 | B1 | 1/2006 | Uitenbroek et al. |
| 6,989,125 | B2 | 1/2006 | Boney et al. |
| 6,992,158 | B2 | 1/2006 | Datta et al. |
| 6,994,763 | B2 | 2/2006 | Austin |
| 7,019,081 | B2 | 3/2006 | Datta et al. |
| 7,022,632 | B2 | 4/2006 | Hatta et al. |
| 7,026,404 | B2 | 4/2006 | Cozewith et al. |
| 7,078,089 | B2 | 7/2006 | Ellis et al. |
| 7,101,622 | B2 | 9/2006 | Chang et al. |
| 7,101,623 | B2 | 9/2006 | Jordan et al. |
| 7,199,203 | B2 | 4/2007 | Stevens et al. |
| 7,261,551 | B2 | 8/2007 | Hutchinson et al. |
| 7,300,895 | B2 | 11/2007 | Kobayashi et al. |
| 7,318,961 | B2 | 1/2008 | Loos et al. |
| 7,319,077 | B2 | 1/2008 | Mehta et al. |
| 7,320,948 | B2 | 1/2008 | Morman et al. |
| 7,329,621 | B2 | 2/2008 | Collier, IV et al. |
| 7,332,204 | B2 | 2/2008 | Hutchinson et al. |
| 7,335,273 | B2 | 2/2008 | Neculescu et al. |
| 7,344,775 | B2 | 3/2008 | Stevens et al. |
| 7,355,089 | B2 | 4/2008 | Chang et al. |
| 7,355,091 | B2 | 4/2008 | Kellenberger et al. |
| 7,404,811 | B2 | 7/2008 | Ohnishi et al. |
| 7,405,171 | B2 | 7/2008 | Tsujiyama et al. |
| 7,405,172 | B2 | 7/2008 | Shigematsu et al. |
| 7,413,803 | B2 | 8/2008 | Jordan et al. |
| 7,425,517 | B2 | 9/2008 | Deka et al. |
| 7,438,777 | B2 | 10/2008 | Pourdeyhimi et al. |
| 7,439,301 | B2 | 10/2008 | Handlin, Jr. |
| 7,445,831 | B2 | 11/2008 | Ashraf et al. |
| 7,445,838 | B2 | 11/2008 | Quinn |
| 7,452,832 | B2 | 11/2008 | Bansal et al. |
| 7,462,573 | B2 | 12/2008 | Tsujiyama et al. |
| 7,476,447 | B2 | 1/2009 | Thomas |
| 7,491,666 | B2 | 2/2009 | Smith et al. |
| 7,494,709 | B2 | 2/2009 | Davis |
| 7,494,947 | B2 | 2/2009 | Boscolo |
| 7,501,034 | B2 | 3/2009 | Ashraf |
| 7,601,666 | B2 | 10/2009 | Rix et al. |
| 7,795,366 | B2 | 9/2010 | Yang et al. |
| 7,867,433 | B2 | 1/2011 | Jacob et al. |
| 8,748,693 | B2 | 6/2014 | Westwood |
| 2002/0019507 | A1 | 2/2002 | Karandinos et al. |
| 2002/0055316 | A1 | 5/2002 | Araida et al. |
| 2003/0125696 | A1 | 7/2003 | Morman et al. |
| 2003/0194939 | A1 | 10/2003 | Schwarz |
| 2004/0110442 | A1 | 6/2004 | Rhim et al. |
| 2004/0121687 | A1 | 6/2004 | Morman et al. |
| 2004/0209540 | A1 | 10/2004 | Schwarz |
| 2004/0236042 | A1 | 11/2004 | Datta et al. |
| 2005/0027080 | A1 | 2/2005 | Bodiford et al. |
| 2005/0106978 | A1 | 5/2005 | Cheng et al. |

(56) References Cited

U.S. PATENT DOCUMENTS

| | | | | |
|---|---|---|---|---|
| 2005/0107529 | A1* | 5/2005 | Datta et al. | 525/70 |
| 2005/0130544 | A1 | 6/2005 | Cheng et al. | |
| 2005/0148263 | A1 | 7/2005 | Zhou et al. | |
| 2005/0170729 | A1 | 8/2005 | Stadelman et al. | |
| 2006/0003658 | A1 | 1/2006 | Hall et al. | |
| 2006/0135923 | A1 | 6/2006 | Boggs et al. | |
| 2006/0141886 | A1 | 6/2006 | Brock et al. | |
| 2006/0151914 | A1 | 7/2006 | Gerndt et al. | |
| 2006/0172647 | A1 | 8/2006 | Mehta et al. | |
| 2006/0173123 | A1 | 8/2006 | Yang et al. | |
| 2006/0199006 | A1 | 9/2006 | Poon et al. | |
| 2006/0210746 | A1 | 9/2006 | Shi et al. | |
| 2006/0270303 | A1 | 11/2006 | Berrigan et al. | |
| 2007/0017075 | A1 | 1/2007 | Nguyen | |
| 2007/0044905 | A1* | 3/2007 | Fitts et al. | 156/244.11 |
| 2007/0078222 | A1 | 4/2007 | Chang et al. | |
| 2007/0092704 | A1 | 4/2007 | Patel et al. | |
| 2007/0123131 | A1 | 5/2007 | Nguyen et al. | |
| 2007/0135785 | A1 | 6/2007 | Qin et al. | |
| 2007/0141937 | A1 | 6/2007 | Hendrix et al. | |
| 2007/0161747 | A1 | 7/2007 | Maier et al. | |
| 2007/0173162 | A1 | 7/2007 | Ethiopia et al. | |
| 2007/0184256 | A1 | 8/2007 | Okada et al. | |
| 2007/0197117 | A1 | 8/2007 | Austin et al. | |
| 2007/0202330 | A1 | 8/2007 | Peng et al. | |
| 2007/0203301 | A1 | 8/2007 | Autran et al. | |
| 2007/0203469 | A1 | 8/2007 | Ohnishi et al. | |
| 2007/0254545 | A1 | 11/2007 | Martin | |
| 2007/0287348 | A1 | 12/2007 | Autran et al. | |
| 2008/0003910 | A1 | 1/2008 | Hughes et al. | |
| 2008/0014819 | A1 | 1/2008 | Suzuki et al. | |
| 2008/0026660 | A1 | 1/2008 | Ogawa et al. | |
| 2008/0038982 | A1 | 2/2008 | Motomura et al. | |
| 2008/0045917 | A1 | 2/2008 | Autran et al. | |
| 2008/0061476 | A1 | 3/2008 | Hutchinson et al. | |
| 2008/0076315 | A1 | 3/2008 | McCormack et al. | |
| 2008/0119102 | A1 | 5/2008 | Hughes et al. | |
| 2008/0132135 | A1 | 6/2008 | Collias et al. | |
| 2008/0132862 | A1 | 6/2008 | Collias et al. | |
| 2008/0132866 | A1 | 6/2008 | Siqueira et al. | |
| 2008/0160859 | A1 | 7/2008 | Gupta et al. | |
| 2008/0160862 | A1 | 7/2008 | Sartori et al. | |
| 2008/0161765 | A1 | 7/2008 | Morman et al. | |
| 2008/0172840 | A1 | 7/2008 | Kacker et al. | |
| 2008/0177242 | A1 | 7/2008 | Chang et al. | |
| 2008/0182116 | A1 | 7/2008 | Dharmarajan et al. | |
| 2008/0182468 | A1 | 7/2008 | Dharmarajan et al. | |
| 2008/0182473 | A1 | 7/2008 | Chen et al. | |
| 2008/0182940 | A1 | 7/2008 | Dharmarajan et al. | |
| 2008/0199673 | A1 | 8/2008 | Allgeuer et al. | |
| 2008/0207071 | A1 | 8/2008 | Muslet et al. | |
| 2008/0220273 | A1 | 9/2008 | Weaver | |
| 2008/0221540 | A1 | 9/2008 | Thomas et al. | |
| 2008/0233819 | A1 | 9/2008 | Tsujiyama et al. | |
| 2008/0233824 | A1 | 9/2008 | Abed et al. | |
| 2008/0237911 | A1 | 10/2008 | Ardiff et al. | |
| 2008/0241447 | A1 | 10/2008 | Shi | |
| 2008/0251492 | A1 | 10/2008 | Shi | |
| 2008/0287027 | A1 | 11/2008 | Suzuki et al. | |
| 2008/0299857 | A1 | 12/2008 | Harding et al. | |
| 2008/0300567 | A1 | 12/2008 | Ohnishi et al. | |
| 2008/0311815 | A1 | 12/2008 | Gupta et al. | |
| 2009/0068419 | A1 | 3/2009 | Pascavage | |
| 2009/0068420 | A1 | 3/2009 | Pascavage | |
| 2009/0124153 | A1 | 5/2009 | Dharmarajan et al. | |
| 2009/0124154 | A1 | 5/2009 | Harrington et al. | |
| 2010/0081352 | A1 | 4/2010 | Westwood | |
| 2010/0124864 | A1 | 5/2010 | Dharmarajan et al. | |
| 2010/0222755 | A1 | 9/2010 | Westwood | |
| 2010/0222761 | A1 | 9/2010 | Westwood et al. | |
| 2010/0266818 | A1 | 10/2010 | Westwood et al. | |
| 2010/0266824 | A1 | 10/2010 | Westwood et al. | |
| 2010/0267914 | A1 | 10/2010 | Westwood et al. | |
| 2011/0081529 | A1 | 4/2011 | Richeson et al. | |
| 2012/0225601 | A1 | 9/2012 | Westwood | |
| 2014/0255672 | A1 | 9/2014 | Westwood | |

FOREIGN PATENT DOCUMENTS

| | | | | |
|---|---|---|---|---|
| EP | 0 129 368 | | | 12/1984 |
| EP | 0212284 | A2 | * | 3/1987 |
| EP | 0 277 003 | | | 8/1988 |
| EP | 0 277 004 | | | 8/1988 |
| EP | 0 426 637 | | | 5/1991 |
| EP | 0 432 755 | | | 6/1991 |
| EP | 0 495 375 | | | 7/1992 |
| EP | 0 500 944 | | | 9/1992 |
| EP | 0 520 732 | | | 12/1992 |
| EP | 0 534 863 | | | 3/1993 |
| EP | 0 570 982 | | | 11/1993 |
| EP | 0 573 403 | | | 12/1993 |
| EP | 1 066 961 | | | 1/2001 |
| EP | 1 070 087 | | | 1/2001 |
| EP | 1 138 472 | | | 10/2001 |
| EP | 1 174 257 | | | 1/2002 |
| EP | 1 614 699 | | | 1/2006 |
| EP | 1 712 351 | | | 10/2006 |
| EP | 1 834 015 | | | 9/2007 |
| EP | 1 877 237 | | | 1/2008 |
| EP | 1 980 390 | | | 10/2008 |
| JP | 09-078431 | A | * | 3/1997 |
| JP | 02/105833 | | | 4/2002 |
| JP | 2005/171456 | | | 6/2005 |
| JP | 2007-154400 | A | * | 6/2007 |
| JP | 4753852 | | | 8/2007 |
| WO | WO 91/09882 | | | 7/1991 |
| WO | WO 92/00333 | | | 1/1992 |
| WO | WO 92/16361 | | | 10/1992 |
| WO | WO 92/16366 | | | 10/1992 |
| WO | WO 94/03506 | | | 2/1994 |
| WO | WO 94/26816 | | | 11/1994 |
| WO | WO 98/39384 | | | 9/1998 |
| WO | WO 00/01745 | | | 1/2000 |
| WO | WO 00/18994 | | | 4/2000 |
| WO | WO 00/37723 | | | 6/2000 |
| WO | WO 00/38911 | | | 7/2000 |
| WO | WO 01/00915 | | | 1/2001 |
| WO | WO 01/00917 | | | 1/2001 |
| WO | WO 02/34511 | | | 5/2002 |
| WO | WO 02/36651 | | | 5/2002 |
| WO | WO 03/040201 | | | 5/2003 |
| WO | WO 2004/038078 | | | 5/2004 |
| WO | WO 2005/049672 | | | 6/2005 |
| WO | WO 2006/101631 | | | 9/2006 |
| WO | WO 2007/030170 | | | 3/2007 |
| WO | WO 2007/140163 | | | 12/2007 |
| WO | WO 2007/142736 | | | 12/2007 |
| WO | WO 2008/094337 | | | 8/2008 |
| WO | WO 2009/064583 | | | 5/2009 |
| WO | WO 2009/126712 | | | 10/2009 |
| WO | WO 2010/001273 | | | 1/2010 |
| WO | WO 2010/039579 | | | 4/2010 |
| WO | WO 2010/039583 | | | 4/2010 |
| WO | WO 2010/098792 | | | 9/2010 |
| WO | WO 2010/098793 | | | 9/2010 |
| WO | WO 2011/041575 | | | 4/2011 |

OTHER PUBLICATIONS

Dutta, S. et al., *"More Efficient Manufacture of Controlled-rheology Polypropylene"*, Society of Plastics Engineers, Plastics Research Online (2010).

Harrington, B.A. et al., *"Processability and Fabric Attributes of Specialty Polyolefin* Elastomers", INTC® 2005, International Nonwovens Technical Conference, Conference Proceedings, St. Louis, MS, United States, Sep. 19-22, 2005.

Kacker, S. et al., *"Properties of Elastic Nonwoven Fabrics Based Upon Specialty Polyolefin Elastomers"*, INTC® 2006, International Nonwovens Technical Conference, Conference Proceedings, Houston, TX, United States, Sep. 25-28, 2006.

(56) References Cited

OTHER PUBLICATIONS

Srivatsan, S. et al., *"Novel Polyolefin Resin for Elastic Spunbond & Melt Blown Applications"*, INTC® 2004, Toronto, Canada, Sep. 20-23, 2004.
VISTAMAXX™ 2120 Propylene-based Elastomer, data sheets. <URL: www.specialtyelastomers.com>.
VISTAMAXX™ Specialty Elastomers for Meltblown Fabrics, data sheet. <URL: www.vistamaxxelastomers.com.
VISTAMAXX™ Specialty Elastomers VM2320, data sheet. <URL: www.vistamaxxelastomers.com.
VISTAMAXX™ Specialty Elastomers for Spunbond Fabrics, data sheet. URL: www.vistamaxxelastomers.com.
VISTAMAXX™ Specialty Elastomers—Unlimited Creative Potential. Imagine That! URL: www.vistamaxxelastomers.com.
Wheeler, L.M. et al., *"Gel Permeation Chromatography/Fourier Transform Infrared Interface for Polymer Analysis"*, Applied Spectroscopy, vol. 47, No. 8, pp. 1128-1130 (1993).
Barden, B., *"Coated Fabrics"*, Kirk-Othmer Encyclopedia of Chemical Technology, John Wiley & Sons, pp. 1-13 (1993).
Rooney, J.G. et al., *"On Line Determination by Light Scattering of Mechanical Degradation in the GPC Process"*, Liquid Chromatography of Polymers and Related Materials III, Cazes, J. Ed., Marcel Dekker, pp. 207-234 (1981).
Chapman, R., *"Nonwoven Fabrics, Staple Fibers"*, Kirk-Othmer Encyclopedia of Chemical Technology, John Wiley & Sons, pp. 1-27 (2005).
Cheng, H. N. "$^{13}$ *C NMR Analysis of Ethylene-Propylene Rubbers"*, Macromolecules, vol. 17, pp. 1950-1955 (1984).
Index05 Daily News, Apr. 14, 2005, in association with Nonwovens Report International, pp. 4.
Index08, Geneva Palexpo, Apr. 15-18, 2008, Biax-Fiberfilm Corporation.
E. P. Moore, Jr. ed., "9.2.1.1 Melt-Blown Fibers," in Polypropylene Handbook, Polymerization, Charaterization, Properties, Processing, Applications, pp. 314-324.
Prabhu, P. et al., *"Evidence for Ethylene-Propylene Block Copolymer Formation"*, J. Poly. Sci.: Polymer Letters Ed., vol. 18, pp. 389-394 (1980).
Rudnick, L.R. et al., *"Poly(α-olefins)"*, Synthetic Lubricants and High Performance Functional Fluids, $2^{nd}$ Edition, Marcel Dekker, Inc., pp. 3-52 (1999).
Seyam, A.M.et al., *"An Examination of the Hydroentangling Process Variables"*, in Int'l Nonwovens J., pp. 25-33 (Spring 2005).
Ver Strate, G. et al., *"Near Monodisperse Ethylene-Propylene Copolymers by Direct Ziegler-Natta Polymerization. Preparation, Characterization, Properties"*, Macromolecules, vol. 21, pp. 3360-3371 (1988).
Zhao, R., *"Melt Blowing Polyoxymethylene Copolymer"*, in Int'l Nonwovens J., pp. 19-24 (Summer 2005).
Zhao, R., "Stretching the Value of Melt Blown with Cellulose Microfiber and Elastic Resin," A Paper for Insight 2004, Austin, Texas, USA, Oct. 10-14, 2004, Biax Fiberfilm Corporation, Greenville, Wisconsin, pp. 1-13.

* cited by examiner

METHOD FOR PRODUCING TEMPERATURE RESISTANT NONWOVENS

CROSS REFERENCE TO RELATED APPLICATIONS

This application relates to concurrently filed U.S. Ser. No. 12/723,336 (2010 EM 171 ), U.S. Ser. No. 12/566,564, filed Sep. 24, 2009; U.S. Ser. No. 61/101,341, filed Sep. 30, 2008; U.S. Ser. No. 12/566,410, filed Sep. 24, 2009; U.S. Ser. No. 61/156,078, filed Feb. 27, 2009; U.S. Ser. No. 12/566,434, filed Sep. 24, 2009; U.S. Ser. No. 61/171,145, filed Apr. 21, 2009; U.S. Ser. No. 12/271,526, filed Nov. 14, 2008; and U.S. Ser. No. 61/157,524, filed Mar. 4, 2009, the disclosures of which are herein incorporated by reference in their entirety.

FIELD OF THE INVENTION

Embodiments of the present invention generally relate to nonwoven fabrics. More particularly, embodiments of the present invention relate to a method for forming temperature resistant nonwoven fabrics with discrete elastic and plastic regions in the plane of the fabric.

BACKGROUND OF THE INVENTION

Elastomers are useful as elastic nonwovens or films in applications ranging from waistbands, side panels, closure systems, and chasses for baby diapers, adult incontinence and personal hygiene garments, as well as other applications. Most of these elastic closures are constructed with facing layers that include a nonwoven substrate that is plastic in properties and provides aesthetic attributes such as touch and feel. Examples of such include those disclosed in U.S. Patent Publication No. 2008/0045917 and its counterparts. The plastic facing layers sandwich the elastic (core) layer, which is inherently elastomeric and possesses a rubbery feel that is not desirable for skin contact.

More recently, highly elastic, breathable, nonwoven fabric with the necessary aesthetic qualities that require no form of mechanical activation have been desired. Existing products are complex laminates of an elastic film, and are typically a styrenic block copolymer ("SBC") or polyurethane as the elastic film that can have polyolefin skins coextruded onto the film to prevent blocking, and nonwovens in order to provide the correct aesthetic (a soft, fluffy, cushion-like texture) and in certain constructions a hot melt glue layer to bond the nonwoven to either side of the elastic film. These types of constructions, once formed, are often not elastic due to the constraining influence of the inelastic components such as the polyolefin skin layers, adhesive, and nonwoven facing layers.

In order to remove the constraining influence of non-elastic elements, many composites require a mechanical stretching or activation process in order to stretch or break the non-elastic components. The mechanical stretching removes the constraints and creates an elastic composite controlled by the SBC film. Furthermore, such composites require the film to be apertured or perforated to make these laminates breathable. This process involves the controlled puncturing/tearing of the film with the associated concerns for film failure and increased scrap rates.

Work in this area has been discussed in U.S. Pat. Nos. 5,272,003; 5,366,782; 6,075,179; 6,342,565; 7,026,404; U.S. Patent Publication Nos. 2008/0199673; 2008/0182116; 2008/0182940; 2008/0182468; 2006/0172647; 2005/0130544; 2005/0106978; and PCT International Publication No. WO 2008/094337. There is still a need, however, for new fabrics and methods for making the same that can provide different performance attributes in a single fabric without activation processes being essential for product performance.

SUMMARY OF THE INVENTION

Temperature resistant multilayer composites, methods for making same, and articles made therefrom are provided. In at least one specific embodiment, the method can include extruding one or more polyolefin polymers having a MFR from less than 90 dg/min through at least one die having a plurality of nozzles to form a plurality of continuous fibers, at least one die operating at a melt pressure from greater than 500 psi (3.45 MPa) to form at least one elastic meltblown layer; adhering the at least one elastic meltblown layer to at least one extensible layer to form a multilayer composite; and at least partially crosslinking the elastic meltblown layer or the extensible layer or both.

In at least one other specific embodiment, the method can include extruding one or more elastic or extensible resins through one or more dies having a plurality of nozzles to form a first plurality of continuous fibers; extruding one or more inelastic resins or extensible through one or more dies simultaneously or nearly simultaneously with the one or more elastic resins to form a second plurality of continuous fibers; and crosslinking the extruded resin using electron beam radiation having an e-beam dose of about 200 kGy (Kilogray) or less.

DETAILED DESCRIPTION

Figure 1:
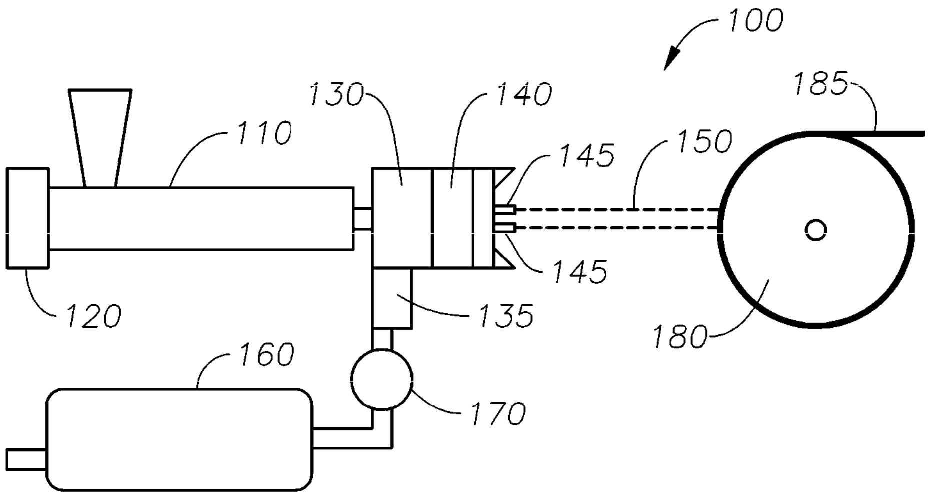
FIG. 1 depicts a schematic view of an illustrative meltblowing system for making a multilayer meltblown composite, according to one or more embodiments described.

The temperature resistant nonwoven fabric can be a multilayer composite or laminate. For example, the temperature resistant nonwoven fabric can be a multilayer composite or laminate that includes at least two meltblown layers made in-situ. Each layer can be extensible, elastic, or inelastic. Each meltblown layer can include one or more resins that are the same or different. Suitable resins for any given layer can also be a blend of two or more resins, where each resin in extensible, inelastic, or elastic, such that the resulting blend can be extensible, inelastic, or elastic, depending on the chosen resins and their relatives amounts.

In one or more embodiments, the temperature resistant nonwoven fabric can further include one or more woven layers. In one or more embodiments, the temperature resistant nonwoven fabric can further include one or more spunlace, spunbond, spunlaid, textiles, air laid, pulp, super-absorbent polymer(s) ("SAP"), and/or film layers. Preferably, at least two meltblown layers are disposed adjacent to one another, and if present, the one or more woven, spunlace, spunbond, spunlaid, textiles, air laid, pulp, SAP, and/or film layers are disposed on or between other meltblown layers.

As used herein, a "composite" or "fabric" is a structure, preferably flat but bendable and otherwise formable, having a thickness such that it impedes, but does not stop, the passage of air, the structure made from fibers that are bound together through chemical bonding, melt adhesion or weaving (mechanical linkage) such that they form the structure. As used herein, a "fiber" is a material whose length is very much greater than its diameter or breadth: the average diameter is on the order of 5 to 250 μm, and includes natural and/or synthetic substances.

As used herein, materials, resins, fibers, and/or fabrics referred to as being "elastic" are those that can recover at least 70% after 100% deformation. As used herein, materials, resins, fibers, and/or fabrics referred to as being "inelastic" are those that can recover less than 20% after 100% deformation. As used herein, materials, resins, fibers, and/or fabrics referred to as being "extensible" are those that can recover 20% to 70% after 100% deformation, as determined by ASTM D412. Extensible materials and fabrics are well known in the art and are those formed, in one instance, from a material that is extensible or by mechanically distorting or twisting a fabric (natural or synthetic) such as described in U.S. Pat. No. 5,523,141.

Suitable resins can be or include cellulosics, nylons, polyacetals, polyalkylene naphthalates, polyesters, co-polyesters, polyurethane, polyamids, polyamides, polyolefins, polyolefin homopolymers, polyolefin copolymers, acrylic, and blends thereof. Except as stated otherwise, the term "copolymer" means a polymer derived from two or more monomers (including terpolymers, tetrapolymers, etc. that can be arranged in a random, block, or grafted distribution), and the term "polymer" refers to any carbon-containing compound having repeat units from one or more different monomers.

Preferred cellulosic materials include rayon and viscose. A preferred polyacetal is polyoxymethylene copolymer. Preferred polyesters include polyolefin-terephthalates and polyalkylene terephthalates, such as poly(ethylene terephthalate) (PET), poly(butylene terephthalate) (PBT), and poly(cyclohexane dimethylene terephthalate) (PCT).

Preferred polyolefins can be prepared from mono-olefin monomers including, but not limited to, monomers having 2 to 8 carbon atoms, such as ethylene, propylene, 1-butene, isobutylene, 1-pentene, 1-hexene, 1-octene, 3-methyl-1-pentene, 4-methyl-1-pentene, 5-methyl-1-hexene, mixtures thereof and copolymers thereof with (meth)acrylates and/or vinyl acetates. Other suitable polyolefins can include one or more propylene homopolymers (100 wt % propylene-derived units), propylene copolymers, propylene-α-olefin copolymers, polypropylene impact copolymers (ICP), random copolymers (RCP) linear low density polyethylene, high density polyethylene, low density polyethylene, ethylene block copolymers (e.g., Infuse™ olefin block copolymers), styrenic block copolymers (e.g., Kraton™ styrenic copolymers), ethylene vinylacetates, urethanes, polyesters, and blends thereof. Certain specific extensible resins can include polyacrylonitrile, polybutylene terephthalate, PET, PCT, polyamide, and/or acrylic.

As used herein, "polypropylene" refers to a propylene homopolymer, or a copolymer of propylene, or some mixture of propylene homopolymers and copolymers. In certain embodiments, the polypropylene described herein is predominately crystalline, thus the polypropylene may have a melting point ($T_m$) greater than 110° C. or 115° C. or 130° C. The term "crystalline," as used herein, characterizes those polymers which possess high degrees of inter-and intra-molecular order. In certain embodiments the polypropylene has a heat of fusion ($H_f$) greater than 60 J/g or 70 J/g or 80 J/g, as determined by Differential Scanning Calorimetry (DSC) analysis. The $H_f$ is dependent on the composition of the polypropylene; the thermal energy for the highest order of polypropylene is estimated at 189 J/g that is, 100% crystallinity is equal to a $H_f$ of 189 J/g. A polypropylene homopolymer will have a higher $H_f$ than a copolymer or blend of homopolymer and copolymer.

In certain embodiments, the polypropylene(s) can be isotactic. Isotacticity of the propylene sequences in the polypropylenes can be achieved by polymerization with the choice of a desirable catalyst composition. The isotacticity of the polypropylenes as measured by $^{13}C$ NMR, and expressed as a meso diad content is greater than 90% (meso diads [m]>0.90) or 95% or 97% or 98% in certain embodiments, determined as in U.S. Pat. No. 4,950,720 by $^{13}C$ NMR. Expressed another way, the isotacticity of the polypropylenes as measured by $^{13}C$ NMR, and expressed as a pentad content, is greater than 93% or 95% or 97% in certain embodiments.

The polypropylene can vary widely in composition. For example, substantially isotactic polypropylene homopolymer or propylene copolymer containing equal to or less than 10 wt % of other monomer, that is, at least 90 wt % propylene can be used. Further, the polypropylene can be present in the form of a graft or block copolymer, in which the blocks of polypropylene have substantially the same stereoregularity as the propylene-α-olefin copolymer (described below) so long as the graft or block copolymer has a sharp melting point above 110° C. or 115° C. or 130° C., characteristic of the stereoregular propylene sequences.

The polypropylene can be a combination of homopolypropylene, and/or random, and/or block copolymers as described herein. When the polypropylene is a random copolymer, the percentage of the α-olefin derived units in the copolymer is, in general, up to 5 wt % of the polypropylene, 0.5 wt % to 5 wt % in another embodiment, and 1 wt % to 4 wt % in yet another embodiment. The preferred comonomer derived from ethylene or α-olefins containing 4 to 12 carbon atoms. One, two or more comonomers can be copolymerized with propylene. Exemplary α-olefins may be selected from the group consisting of: ethylene; 1-butene; 1-pentene-2-methyl-1-pentene-3-methyl-1-butene; 1-hexene-3-methyl-1-pentene-4-methyl-1-pentene-3,3-dimethyl-1-butene; 1-heptene; 1-hexene; 1-methyl-1-hexene; dimethyl-1-pentene; trimethyl-1-butene; ethyl-1-pentene; 1-octene; methyl-1-pentene; dimethyl-1-hexene; trimethyl-1-pentene; ethyl-1-hexene; 1-methylethyl-1-pentene; 1-diethyl-1-butene; propyl-1-pentene; 1-decene; methyl-1-nonene; 1-nonene; dimethyl-1-octene; trimethyl-1-heptene; ethyl-1-octene; methylethyl-1-butene; diethyl-1-hexene; 1-dodecene; and 1-hexadodcene.

The weight average molecular weight (Mw) of the polypropylene can be between 50,000 g/mol to 3,000,000 g/mol, or from 90,000 g/mol to 500,000 g/mol in another embodiment, with a molecular weight distribution (MWD, Mw/Mn) within the range from 1.5 to 2.5; or 3.0 to 4.0; or 5.0 to 20.0. The polypropylene can have an MFR (2.16 kg/230° C.) ranging of from 10 dg/min to 15 dg/min; or 18 dg/min to 30 dg/min; or 35 dg/min to 45 dg/min; or 40 dg/min to 50 dg/min.

The term “random polypropylene” (“RCP”) as used herein broadly means a single phase copolymer of propylene having up to 9 wt %, preferably 2 wt % to 8 wt % of an alpha olefin comonomer. Preferred alpha olefin comonomers have 2 carbon atoms, or from 4 to 12 carbon atoms. Preferably, the alpha olefin comonomer is ethylene.

The propylene impact copolymers (“ICP”) is heterogeneous and can include a first phase of 70 to 95 wt % homopolypropylene and a second phase of from 5 wt % to 30 wt % ethylene-propylene rubber, based on the total weight of the impact copolymer. The propylene impact copolymer can include 78 wt % to 95 wt % homopolypropylene and from 5 wt % to 22 wt % ethylene-propylene rubber, based on the total weight of the impact copolymer. In certain embodiments, the impact copolymer can include from 90 wt % to 95 wt % homopolypropylene and from 5 wt % to 10 wt % ethylene-propylene rubber, based on the total weight of the impact copolymer.

There is no particular limitation on the method for preparing the polypropylenes described herein. However, for example, the polymer is a propylene homopolymer obtained by homopolymerization of propylene in a single stage or multiple stage reactor. Copolymers may be obtained by copolymerizing propylene and ethylene or an α-olefin having from 4 to 20 carbon atoms in a single stage or multiple stage reactor. Polymerization methods include, but are not limited to, high pressure, slurry, gas, bulk, or solution phase, or a combination thereof, using any suitable catalyst such as traditional Ziegler-Natta catalyst or a single-site, metallocene catalyst system, or combinations thereof including bimetallic (i.e., Ziegler-Natta and metallocene) supported catalyst systems.

Exemplary commercial polypropylenes include the family of Achieve™ polymers (ExxonMobil Chemical Company, Baytown, Tex.). The Achieve polymers are produced using metallocene catalyst systems. In certain embodiments, the metallocene catalyst system produces a narrow molecular weight distribution polymer. The MWD is typically in the range of 1.5 to 2.5. However, a broader MWD polymer may be produced in a process with multiple reactors. Different MW polymers can be produced in each reactor to broaden the MWD. Achieve polymer such as Achieve 3854, a homopolymer having an MFR of 24 dg/min can be used as a blend component described herein. Alternatively, an Achieve polymer such as Achieve 6936G1, a 1550 dg/min MFR homopolymer, can be used as a blend component described herein. Other polypropylene random copolymer and impact copolymer may also be used. The choice of polypropylene MFR can be used as means of adjusting the final MFR of the blend, especially the facing layer composition. Any of the polypropylenes described herein can be modified by controlled rheology to improve spinning performance as is known in the art.

The “propylene-α-olefin copolymer” is a copolymer of propylene-derived units and one or more units derived from ethylene or a $C_4$-$C_{10}$ α-olefin and optionally one or more diene-derived units, and are relatively elastic and/or form nonwoven fibers and fabrics that are elastic (Ultimate Elongation from greater than 500%). The overall comonomer content of the copolymer is within the range from 5 to 35 wt % in one embodiment. In some embodiments, where more than one comonomer is present, the amount of a particular comonomer may be less than 5 wt %, but the combined comonomer content is from greater than 5 wt %. The propylene-α-olefin copolymers may be described by any number of different parameters, and those parameters may include a numerical range made up of any desirable upper limit with any desirable lower limit as described herein for the propylene-α-olefin copolymers.

The propylene-α-olefin copolymer may be a terpolymer of propylene, block copolymer (the comonomer-derived units occur along long sequences), impact copolymer of propylene, random polypropylene, random copolymer (the comonomer-derived units are randomly distributed along the polymer backbone), or mixtures thereof. The presence of randomness or “blocky-ness” in a copolymer can be determined by $^{13}C$ NMR as is known in the art and described in, for example, 18 J. Poly. Sci.: Poly. Lett. Ed. 389-394 (1980).

In certain embodiments, the propylene-α-olefin copolymer can include ethylene or $C_4$-$C_{10}$ α-olefin-derived units (or “comonomer-derived units”) within the range from 5 wt % or 7 wt % or 8 wt % or 10 wt % to 18 wt % or 20 wt % or 25 wt % or 32 wt % or 35 wt % of the copolymer. The propylene-α-olefin copolymer may also include two different comonomer-derived units. Also, these copolymers and terpolymers may include diene-derived units as described below. In a particular embodiment, the propylene-α-olefin copolymer includes propylene-derived units and comonomer units selected from ethylene, 1-butene, 1-hexene, and 1-octene. And in a more particular embodiment, the comonomer is ethylene, and thus the propylene-α-olefin copolymer is a propylene-ethylene copolymer.

The propylene-α-olefin copolymer can be or include one or more propylene-α-olefin-diene terpolymers or propylene-diene copolymers. For example, the propylene-α-olefin copolymer can be prepared by polymerizing propylene with one or more dienes. In at least one other specific embodiment, the propylene-α-olefin copolymer can be prepared by polymerizing propylene with ethylene and/or at least one $C_4$-$C_{20}$ α-olefin, or a combination of ethylene and at least one $C_4$-$C_{20}$ α-olefin and one or more dienes. The one or more dienes can be conjugated or non-conjugated. Preferably, the one or more dienes are non-conjugated.

The comonomers can be linear or branched. Preferred linear comonomers include ethylene or $C_4$ to $C_8$ α-olefins, more preferably ethylene, 1-butene, 1-hexene, and 1-octene, even more preferably ethylene, or 1-butene. Preferred branched comonomers include 4-methyl-1-pentene, 3-methyl-1-pentene, and 3,5,5-trimethyl-1-hexene. In one or more embodiments, the comonomer can include styrene.

Illustrative dienes can include but are not limited to 5-ethylidene-2-norbornene (ENB); 1,4-hexadiene; 5-methylene-2-norbornene (MNB); 1,6-octadiene; 5-methyl-1,4-hexadiene; 3,7-dimethyl-1,6-octadiene; 1,3-cyclopentadiene; 1,4-cyclohexadiene; vinyl norbornene (VNB); dicyclopendadiene (DCPD); and combinations thereof. Preferably, the diene is ENB.

Preferred methods and catalysts for producing the propylene-α-olefin copolymers are found in publications US 2004/0236042 and WO 05/049672 and in U.S. Pat. No. 6,881,800, which are all incorporated by reference herein. Pyridine amine complexes, such as those described in PCT International Publication No. WO 03/040201 are also useful to produce the propylene-α-olefin copolymers useful herein. The catalyst can involve a fluxional complex, which undergoes periodic intra-molecular re-arrangement so as to provide the desired interruption of stereoregularity as in U.S. Pat. No. 6,559,262. The catalyst can be a stereorigid complex with mixed influence on propylene insertion, see Rieger, European Patent No. 1070087. The catalyst described in European Patent No. 1614699 could also be used for the production of backbones suitable for the invention.

The propylene-α-olefin copolymer can have an average propylene content on a weight percent basis of from about 60 wt % to about 99.7 wt %, more preferably from about 60 wt % to about 99.5 wt %, more preferably from about 60 wt % to about 97 wt %, more preferably from about 60 wt % to about 95 wt % based on the weight of the polymer. In one embodiment, the balance comprises diene. In another embodiment, the balance comprises one or more dienes and one or more of the α-olefins described previously. Other preferred ranges are from about 80 wt % to about 95 wt % propylene, more preferably from about 83 wt % to about 95 wt % propylene, more preferably from about 84 wt % to about 95 wt % propylene, and more preferably from about 84 wt % to about 94 wt % propylene based on the weight of the polymer.

Preferably, the propylene-α-olefin copolymer comprises about 0.2 wt % to about 24 wt %, of a non-conjugated diene based on the weight of the polymer, more preferably from about 0.5 wt % to about 12 wt %, more preferably about 0.6 wt % to about 8 wt %, and more preferably about 0.7 wt % to about 5 wt %. In other embodiments, the diene content ranges from about 0.2 wt % to about 10 wt %, more preferably from about 0.2 wt % to about 5 wt %, more preferably from about 0.2 wt % to about 4 wt %, preferably from about 0.2 wt % to about 3.5 wt %, preferably from about 0.2 wt % to about 3.0 wt %, and preferably from about 0.2 wt % to about 2.5 wt % based on the weight of the polymer. In one or more embodiments above or elsewhere herein, the propylene-α-olefin copolymer comprises ENB in an amount of from about 0.5 wt % to about 4 wt %, more preferably from about 0.5 wt % to about 2.5 wt %, and more preferably from about 0.5 wt % to about 2.0 wt %.

In other embodiments, the propylene-α-olefin copolymer preferably comprises propylene and diene in one or more of the ranges described above with the balance comprising one or more $C_2$ and/or $C_4$-$C_{20}$ olefins. In general, this will amount to the propylene-α-olefin copolymer preferably comprising from about 5 wt % to about 40 wt % of one or more $C_2$ and/or $C_4$-$C_{20}$ olefins based the weight of the polymer. When $C_2$ and/or a $C_4$-$C_{20}$ olefins are present the combined amounts of these olefins in the polymer is preferably at least about 5 wt % and falling within the ranges described herein. Other preferred ranges for the one or more α-olefins include from about 5 wt % to about 35 wt %, more preferably from about 5 wt % to about 30 wt %, more preferably from about 5 wt % to about 25 wt %, more preferably from about 5 wt % to about 20 wt %, more preferably from about 5 wt % to about 17 wt % and more preferably from about 5 wt % to about 16 wt %.

In certain embodiments, the propylene-α-olefin copolymers have a triad tacticity of three propylene units, as measured by $^{13}C$ NMR, from greater than 75% or 80% or 82% or 85% or 90%. In one embodiment, the triad tacticity is within the range from 50% to 99%, and from 60% to 99%, in another embodiment, and from 75% to 99%, in yet another embodiment, and from 80% to 99%, in yet another embodiment; and from 60% to 97%, in yet another embodiment. Triad tacticity is determined as follows: The tacticity index, expressed herein as "m/r", is determined by $^{13}C$ NMR. The tacticity index m/r is calculated as defined by H. N. Cheng, "$^{13}C$ NMR Analysis of Ethylene-Propylene Rubbers," in Vol. 17, Issue 10, Macromolecules, pp. 1950-1955 (October 1984). The designation "m" or "r" describes the stereochemistry of pairs of contiguous propylene groups, "m" referring to meso and "r" to racemic. An m/r ratio of 1.0 generally describes a syndiotactic polymer, and an m/r ratio of 2.0 an atactic material. An isotactic material theoretically may have a ratio approaching infinity, and many by-product atactic polymers have sufficient isotactic content to result in ratios from greater than 50. Embodiments of the propylene-α-olefin copolymer have a tacticity index m/r within the range from 4 or 6 to 8 or 10 or 12.

In certain embodiments, the propylene-α-olefin copolymers have a $H_f$, determined according to the DSC procedure described herein, within the range from 0.5 or 1 or 5 J/g, to 35 or 40 or 50 or 65 or 75 J/g. In certain embodiments, the $H_f$ value is from less than 75 or 65 or 55 J/g.

In certain embodiments, the propylene-α-olefin copolymers have a percent crystallinity within the range from 0.5% to 40%, and from 1% to 30% in another embodiment, and from 5% to 25% in yet another embodiment, wherein "percent crystallinity" is determined according to the DSC procedure described herein. (The thermal energy for the highest order of polypropylene is estimated at 189 J/g (i.e., 100% crystallinity is equal to 189 J/g).) In another embodiment, the propylene-α-olefin copolymer has a percent crystallinity from less than 40% or 25% or 22% or 20%.

In certain embodiments, the propylene-α-olefin copolymers have a single peak melting transition as determined by DSC; in certain embodiments the propylene-α-olefin copolymer has a primary peak melting transition from less than 90° C., with a broad end-of-melt transition from greater than about 110° C. The peak $T_m$ is defined as the temperature of the greatest heat absorption within the range of melting of the sample. However, the propylene-α-olefin copolymer may show secondary melting peaks adjacent to the principal peak, and/or the end-of-melt transition, but for purposes herein, such secondary melting peaks are considered together as a single melting point, with the highest of these peaks being considered the $T_m$ of the propylene-α-olefin copolymer. The propylene-α-olefin copolymers have a peak melting temperature ($T_m$) from less than 70 or 80 or 90 or 100 or 105° C. in certain embodiments; and within the range from 10 or 15 or 20 or 25 to 65 or 75 or 80 or 95 or 105° C. in other embodiments.

The procedure for DSC determinations is as follows. About 0.5 grams of polymer is weighed out and pressed to a thickness of about 15-20 mils (about 381-508 microns) at about 140° C. -150° C., using a "DSC mold" and Mylar™ as a backing sheet. The pressed pad is allowed to cool to ambient temperature by hanging in air (the Mylar was not removed).

The pressed pad is annealed at room temperature (about 23° C.-25° C.) for about 8 days. At the end of this period, an about 15-20 mg disc is removed from the pressed pad using a punch die and placed in a 10 microliter aluminum sample pan. The sample is placed in a differential scanning calorimeter (Perkin Elmer Pyris 1 Thermal Analysis System) and cooled to about −100° C. The sample is heated at about 10° C./min to attain a final temperature of about 165° C. The thermal output, recorded as the area under the melting peak of the sample, is a measure of the heat of fusion and can be expressed in Joules per gram (J/g) of polymer and automatically calculated by the Perkin Elmer System. Under these conditions, the melting profile shows two (2) maxima, the maxima at the highest temperature was taken as the melting point within the range of melting of the sample relative to a baseline measurement for the increasing heat capacity of the polymer as a function of temperature.

In certain embodiments, the propylene-α-olefin copolymers have a density within the range from 0.840 $g/cm^3$ to 0.920 $g/cm^3$; and from 0.845 $g/cm^3$ to 0.900 $g/cm^3$, in another embodiment; and from 0.850 $g/cm^3$ to 0.890 $g/cm^3$, in yet another embodiment; the values measured at room temperature per the ASTM D-1505 test method.

In certain embodiments, the propylene-α-olefin copolymers have a Shore A Hardness (ASTM D2240) within the range from 10 or 20 to 80 or 90 Shore A. In yet another embodiment, the propylene-α-olefin copolymers possess an Ultimate Elongation (ASTM-D412) greater than 500%, 1,000% or 2,000%. The propylene-α-olefin copolymers can also have an Ultimate Elongation (ASTM-D412) ranging from a low of about 300%, 400%, or 500% to a high of about 800%, 1,200%, 1,800%, 2,000%, or 3,000%.

In certain embodiments, the propylene-α-olefin copolymers have a Mw value within the range from 20,000 to 5,000,000 g/mole; and from 50,000 to 1,000,000 g/mole, in another embodiment; and from 70,000 to 400,000 g/mole, in yet another embodiment. In another embodiment, the propylene-α-olefin copolymers have a number average molecular weight (Mn) value within the range from 4,500 to 2,500,000 g/mole; and from 20,000 to 250,000 g/mole, in yet another embodiment; and from 50,000 to 200,000 g/mole, in yet another embodiment. In yet another embodiment, the propylene-α-olefin copolymers have a z-average molecular weight (Mz) value within the range from 20,000 to 7,000,000 g/mole; and from 100,000 to 700,000 g/mole, in another embodiment; and from 140,000 to 500,000 g/mole, in yet another embodiment.

In certain embodiments, a desirable molecular weight (and hence, a desirable MFR) is achieved by visbreaking the propylene-α-olefin copolymers. The "visbroken propylene-α-olefin copolymers" (also known in the art as "controlled rheology" or "CR") is a copolymer that has been treated with a visbreaking agent such that the agent breaks apart the polymer chains. Non-limiting examples of visbreaking agents include peroxides, hydroxylamine esters, and other oxidizing and free-radical generating agents. Stated another way, the visbroken copolymer may be the reaction product of a visbreaking agent and the copolymer. In particular, a visbroken propylene-α-olefin copolymer is one that has been treated with a visbreaking agent such that its MFR is increased, in one embodiment by at least 10%, and at least 20% in another embodiment relative to the MFR value prior to treatment.

In certain embodiments, the MWD of the propylene-α-olefin copolymers is within the range from 1.5 or 1.8 or 2.0 to 3.0 or 3.5 or 4.0 or 5.0 or 10.0 in particular embodiments. Techniques for determining the Mn, Mz and Mw and MWD are as follows, and as by Verstate et al. in 21 Macromolecules 3360 (1988). Conditions described herein govern over published test conditions. Mn, Mz and Mw, and MWD are measured using a Waters 150 gel permeation chromatograph equipped with a Chromatix KMX-6 on-line light scattering photometer. The system was used at 135° C. with 1,2,4-trichlorobenzene as the mobile phase. Showdex™ (Showa-Denko America, Inc.) polystyrene gel columns 802, 803, 804 and 805 are used. This technique is discussed in Liquid Chromatography of Polymers and Related Materials III 207 (J. Cazes ed., Marcel Dekker, 1981). No corrections for column spreading were employed; however, data on generally accepted standards, for example, National Bureau of Standards, Polyethylene (SRM 1484) and anionically produced hydrogenated polyisoprenes (an alternating ethylene-propylene copolymer) demonstrate that such corrections on Mw/Mn or Mz/Mw are less than 0.05 units. Mw/Mn was calculated from an elution time-molecular weight relationship whereas Mz/Mw was evaluated using the light scattering photometer. The numerical analyses can be performed using the commercially available computer software GPC2, MOLWT2 available from LDC/Milton Roy-Riviera Beach, Fla.

The propylene-α-olefin copolymers described herein can be produced using any catalyst and/or process known for producing polypropylenes. In certain embodiments, the propylene-α-olefin copolymers can include copolymers prepared according to the procedures in PCT International Publication No. WO 02/36651, U.S. Pat. No. 6,992,158, and/or PCT International Publication No. WO 00/01745. Preferred methods for producing the propylene-α-olefin copolymers are found in U.S. Patent Publication No. 2004/0236042 and U.S. Pat. No. 6,881,800. Preferred propylene-α-olefin copolymers are available commercially under the trade names VISTAMAXX™ (ExxonMobil Chemical Company, Houston, Tex., USA) and VERSIFY™ (The Dow Chemical Company, Midland, Mich., USA), certain grades of TAFMER™ XM or NOTIO™ (Mitsui Company, Japan), certain grades of LMPO™ from Idemitsu, or certain grades of SOFTELL™ (Lyondell Basell Polyolefine GmbH, Germany). A commercial example of an ethylene-based polyolefin block copolymer is INFUSE™ olefin block copolymers from Dow Chemical.

In one or more embodiments, the meltblown resin can be or include: natural rubber (NR); synthetic polyisoprene (IR); butyl rubber (copolymer of isobutylene and isoprene, IIR); halogenated butyl rubbers (chloro-butyl rubber (CIIR); bromo-butyl rubber (BIIR)); polybutadiene (BR); styrene-butadiene rubber (SBR); SEBS block copolymers; SIS block copolymers; SBS block copolymers; ethylene-octene block copolymers; ethylene-octene copolymers; ethylene-hexene copolymers; ethylene-butene copolymers; nitrile rubber; hydrogenated nitrile rubbers; chloroprene rubber (CR); polychloroprene; neoprene; EPM (ethylene-propylene rubber) and EPDM rubbers (ethylene-propylene-diene rubber); epichlorohydrin rubber (ECO); polyacrylic rubber (ACM, ABR); silicone rubber; fluorosilicone rubber; fluoroelastomers; perfluoroelastomers; polyether block amides (PEBA); chlorosulfonated polyethylene (CSM); ethylene-vinyl acetate (EVA); thermoplastic elastomers (TPE); thermoplastic vulcanizates (TPV); thermoplastic polyurethane (TPU); thermoplastic olefins (TPO); polysulfide rubber; or blends of any two or more of these elastomers. In at least one specific embodiment, the elastic resin is or includes one or more polyolefin polymers. The term "polyolefin polymers" refers to homopolymers or copolymers of α-olefins having less than 40% crystallinity, or a $H_f$ of less than 75 J/g.

In certain embodiments, the meltblown resin can be or include one or more metallocene polyethylenes ("mPE's"), including one or more mPE homopolymers or copolymers. The mPE homopolymers or copolymers may be produced using mono- or bis-cyclopentadienyl transition metal catalysts in combination with an activator of alumoxane and/or a non-coordinating anion in solution, slurry, high pressure or gas phase. The catalyst and activator may be supported or unsupported and the cyclopentadienyl rings may be substituted or unsubstituted. Several commercial products produced with such catalyst/activator combinations are commercially available from ExxonMobil Chemical Company in Baytown, Tex. under the tradename EXACT™. For more information on the methods and catalysts/activators to produce such mPE homopolymers and copolymers see PCT International Publication Nos. WO 94/26816; WO 92/00333; WO 91/09882; WO 94/03506; and WO 94/03506; European Patent No(s): 0 277 003; 0 129 368; 0 520 732; 0 426 637; 0 573 403; 0 520 732; 0 495 375; 0 500 944; 0 570982; and 0 277004; U.S. Pat. Nos. 5,153,157; 5,198,401; 5,240,894; 5,324,800; 5,264,405; 5,096,867; 5,507,475; 5,055,438; and 5,017,714; and Canadian Patent No. 1,268,753.

In certain embodiments, the meltblown resin can be or include one or more termonomers and tetramonomers which may be one or more $C_3$-$C_{20}$ olefins, any $C_4$-$C_{20}$ linear, cyclic or branched dienes or trienes and any styrenic monomers such as styrene, alpha-methyl styrene, or para-methyl styrene. Preferred examples include butadiene, pentadiene, cyclopentadiene, hexadiene, cyclohexadiene, heptadiene, octadiene, nonadiene, norbornene, vinyl norbornene, ethylidene norbornene, isoprene and heptadiene.

The $C_3$-$C_{20}$ and $C_4$-$C_{20}$ olefins can be any polymerizable olefin monomer and are preferably a linear, branched or cyclic olefin, even more preferably an alpha-olefin. Examples of suitable olefins include: propylene; butene; isobutylene; pentene; isopentene; cyclopentene; hexane; isohexene; cyclohexene; heptene; isoheptene; cycloheptene; octane; isooctane; cyclooctene; nonene; cyclononene; decene; isodecene; dodecene; isodecene; 4-methyl-pentene-1; 3-methyl-pentene-1; 3,5,5-trimethyl-hexene-1. Suitable comonomers also include: dienes; trienes; and styrenic monomers. Preferred examples include: styrene; alpha-methyl styrene; para-alkyl styrene (such as para-methyl styrene); hexadiene; norbornene; vinyl norbornene; ethylidene norbornene; butadiene; isoprene; heptadiene; octadiene; and cyclopentadiene. Preferred comonomers for the copolymer of ethylene are propylene, butene, hexene and/or octene.

In certain embodiments, the meltblown resin can include one or more polyalphaolefins (PAOs). PAOs are high purity hydrocarbons, with a fully paraffinic structure and a high degree of branching. Suitable PAOs are liquids with a pour point of -10° C. or less and a kinematic viscosity at 100° C. (KV100° C.) of 3 cSt or more. Such PAOs can include $CH_{15}$-$C_{1500}$ (preferably $C_{20}$-$C_{1000}$, preferably $C_{30}$-$C_{800}$, preferably $C_{35}$-$C_{400}$, most preferably $C_{40}$-$C_{250}$) oligomers (such as dimers, trimers, etc.) of $C_3$-$C_{24}$ (preferably $C_5$-$C_{18}$, preferably $C_6$-$C_{14}$, preferably $C_8$-$C_{12}$) alpha-olefins, preferably linear alpha-olefins (LAOs), provided that $C_3$ and $C_4$ alpha-olefins are present at 30 wt % or less (preferably 20 wt % or less, preferably 10 wt % or less, preferably 5 wt % or less). Suitable LAOs include: propylene; 1-butene; 1-pentene; 1-hexene; 1-heptene; 1-octene; 1-nonene; 1-decene; 1-undecene; 1-dodecene; 1-tridecene; 1-tetradecene; 1-pentadecene; 1-hexadecene; and blends thereof.

In one or more embodiments, a single LAO is used to prepare the oligomers. A preferred embodiment involves the oligomerization of 1-octene or 1-decene, preferably 1-decene. In one or more embodiments, the PAO is or includes oligomers of two or more $C_3$-$C_{18}$ LAOS, to make 'bipolymer' or 'terpolymer' or higher-order copolymer combinations, provided that $C_3$ and $C_4$ LAOs are present 30 wt % or less (preferably 20 wt % or less, preferably 10 wt % or less, preferably 5 wt % or less). A preferred embodiment involves oligomerization of a mixture of LAOs selected from $C_6$-$C_{18}$ LAOs with even carbon numbers. Another preferred embodiment involves oligomerization of 1-octene, 1-decene, and 1-dodecene.

In one or more embodiments, the PAO comprises oligomers of a single alpha-olefin species having a carbon number of 5 to 24 (preferably 6 to 18, more preferably 8 to 12, most preferably 10). In one or more embodiments, the PAO comprises oligomers of mixed alpha-olefins (i.e., two or more alpha-olefin species), each alpha-olefin having a carbon number of 5 to 24 (preferably 6 to 18, preferably 8 to 12). In one or more embodiments, the PAO comprises oligomers of mixed alpha-olefins (i.e., involving two or more alpha-olefin species) where the weighted average carbon number for the alpha-olefin mixture is 6 to 14 (preferably 8 to 12, preferably 9 to 11).

In one or more embodiments, the PAO or blend of PAOs has a $M_n$ of from 400 to 15,000 g/mol (preferably 400 to 12,000 g/mol, preferably 500 to 10,000 g/mol, preferably 600 to 8,000 g/mol, preferably 800 to 6,000 g/mol, preferably 1,000 to 5,000 g/mol). In one or more embodiments, the PAO or blend of PAOs has a $M_n$ greater than 1,000 g/mol (preferably greater than 1,500 g/mol, preferably greater than 2,000 g/mol, preferably greater than 2,500 g/mol).

In one or more embodiments, the PAO or blend of PAOs has a KV100° C. of 3 cSt or more (preferably 4 cSt or more, preferably 5 cSt or more, preferably 6 cSt or more, preferably 8 cSt or more, preferably 10 cSt or more, preferably 20 cSt or more, preferably 30 cSt or more, preferably 40 cSt or more, preferably 100 or more, preferably 150 cSt or more). In one or more embodiments, the PAO has a KV100° C. of 3 to 3,000 cSt (preferably 4 to 1,000 cSt, preferably 6 to 300 cSt, preferably 8 to 150 cSt, preferably 8 to 100 cSt, preferably 8 to 40 cSt). In one or more embodiments, the PAO or blend of PAOs has a KV100° C. of 10 to 1000 cSt (preferably 10 to 300 cSt, preferably 10 to 100 cSt). In yet another embodiment, the PAO or blend of PAOs has a KV100° C. of 4 to 8 cSt. In yet another embodiment, the PAO or blend of PAOs has a KV100° C. of 25 to 300 cSt (preferably 40 to 300 cSt, preferably 40 to 150 cSt). In one or more embodiments, the PAO or blend of PAOs has a KV100° C. of 100 to 300 cSt.

In one or more embodiments, the PAO or blend of PAOs has a Viscosity Index (VI) of 120 or more (preferably 130 or more, preferably 140 or more, preferably 150 or more, preferably 170 or more, preferably 190 or more, preferably 200 or more, preferably 250 or more, preferably 300 or more). In one or more embodiments, the PAO or blend of PAOs has a VI of 120 to 350 (preferably 130 to 250).

In one or more embodiments, the PAO or blend of PAOs has a pour point of −10° C. or less (preferably −20° C. or less, preferably −25° C. or less, preferably −30° C. or less, preferably −35° C. or less, preferably −40° C. or less, preferably −50° C. or less). In one or more embodiments, the PAO or blend of PAOs has a pour point of −15 to −70° C. (preferably −25 to −60° C.).

In one or more embodiments, the PAO or blend of PAOs has a glass transition temperature ($T_g$) of −40° C. or less (preferably −50° C. or less, preferably −60° C. or less, preferably −70° C. or less, preferably −80° C. or less). In one or more embodiments, the PAO or blend of PAOs has a $T_g$ of −50 to −120° C. (preferably −60 to −100° C., preferably −70 to −90° C.).

In one or more embodiments, the PAO or blend of PAOs has a flash point of 200° C. or more (preferably 210° C. or more, preferably 220° C. or more, preferably 230° C. or more), preferably between 240° C. and 290° C. In one or more embodiments, the PAO or blend of PAOs has a specific gravity (15.6° C.) of 0.86 or less (preferably 0.855 or less, preferably 0.85 or less, preferably 0.84 or less).

In one or more embodiments, the PAO or blend of PAOs has a $M_w/M_n$ of 2 or more (preferably 2.5 or more, preferably 3 or more, preferably 4 or more, preferably 5 or more, preferably 6 or more, preferably 8 or more, preferably 10 or more). In one or more embodiments, the PAO or blend of PAOs has a $M_w/M_n$ of 5 or less (preferably 4 or less, preferably 3 or less) and a KV100° C. of 10 cSt or more (preferably 20 cSt or more, preferably 40 cSt or more, preferably 60 cSt or more).

Desirable PAOs are commercially available as SpectraSyn™ and SpectraSyn Ultra™ from ExxonMobil Chemical (USA), some of which are summarized in Table A. Other useful PAOs include those available as Synfluid™ from ChevronPhillips Chemical (USA), as Durasyn™ from Innovene (USA), as Nexbase™ from Neste Oil (Finland), and as Synton™ from Chemtura (USA). For PAOs, the percentage of carbons in chain-type paraffinic structures (Cp) is close to 100% (typically greater than 98% or even 99%). Additional details are described in, for example, U.S. Pat. Nos. 3,149,178; 4,827,064; 4,827,073; 5,171,908; and 5,783,531; and in Synthetic Lubricants and High-Performance Functional Fluids (Leslie R. Rudnick & Ronald L. Shubkin, ed. Marcel Dekker, Inc. 1999), pp. 3-52.

Grafted (Functionalized) Backbone

In one or more embodiments, the propylene-α-olefin copolymer can be grafted (i.e., "functionalized") using one or more grafting monomers. As used herein, the term "grafting" denotes covalent bonding of the grafting monomer to a polymer chain of the propylene-α-olefin copolymer.

The grafting monomer can be or include at least one ethylenically unsaturated carboxylic acid or acid derivative, such as an acid anhydride, ester, salt, amide, imide, acrylates or the like. Illustrative monomers include but are not limited to: acrylic acid; methacrylic acid; maleic acid; fumaric acid; itaconic acid; citraconic acid; mesaconic acid; maleic anhydride; 4-methyl cyclohexene-1,2-dicarboxylic acid anhydride; bicyclo(2.2.2)octene-2,3-dicarboxylic acid anhydride; 1,2,3,4,5,8,9,10-octahydronaphthalene-2,3-dicarboxylic acid anhydride; 2-oxa-1,3-diketospiro(4.4)nonene; bicyclo(2.2.1)heptene-2,3-dicarboxylic acid anhydride; maleopimaric acid; tetrahydrophthalic anhydride; norbornene-2,3-dicarboxylic acid anhydride; nadic anhydride; methyl nadic anhydride; himic anhydride; methyl himic anhydride; and 5-methylbicyclo(2.2.1)heptene-2,3-dicarboxylic acid anhydride. Other suitable grafting monomers include: methyl acrylate and higher alkyl acrylates; methyl methacrylate and higher alkyl methacrylates; acrylic acid; methacrylic acid; hydroxy-methyl methacrylate; hydroxyl-ethyl methacrylate and higher hydroxy-alkyl methacrylates and glycidyl methacrylate. Maleic anhydride is a preferred grafting monomer.

In one or more embodiments, the grafted propylene based polymer comprises from about 0.5 wt % to about 10 wt % ethylenically unsaturated carboxylic acid or acid derivative, more preferably from about 0.5 wt % to about 6 wt %, more preferably from about 0.5 wt % to about 3 wt %; in other embodiments from about 1 wt % to about 6 wt %, more preferably from about 1 wt % to about 3 wt %. In a preferred embodiment wherein the graft monomer is maleic anhydride, the maleic anhydride concentration in the grafted polymer is preferably in the range of about 1 wt % to about 6 wt %, preferably at least about 0.5 wt % and highly preferably about 1.5 wt %.

Styrene and derivatives thereof such as paramethyl styrene, or other higher alkyl substituted styrenes such as t-butyl styrene can be used as a charge transfer agent in presence of the grafting monomer to inhibit chain scissioning. This allows further minimization of the beta scission reaction and the production of a higher molecular weight grafted polymer (MFR=1.5).

Preparing Grafted Propylene-α-olefin Copolymers

The grafted propylene-α-olefin copolymer can be prepared using conventional techniques. For example, the graft polymer can be prepared in solution, in a fluidized bed reactor, or by melt grafting. A preferred grafted polymer can be prepared by melt blending in a shear-imparting reactor, such as an extruder reactor. Single screw but preferably twin screw extruder reactors such as co-rotating intermeshing extruder or counter-rotating non-intermeshing extruders but also co-kneaders such as those sold by Buss are especially preferred.

In one or more embodiments, the grafted polymer can be prepared by melt blending the ungrafted propylene-α-olefin copolymer with a free radical generating catalyst, such as a peroxide initiator, in the presence of the grafting monomer. The preferred sequence for the grafting reaction includes melting the propylene-α-olefin copolymer, adding and dispersing the grafting monomer, introducing the peroxide and venting the unreacted monomer and by-products resulting from the peroxide decomposition. Other sequences can include feeding the monomers and the peroxide pre-dissolved in a solvent.

Illustrative peroxide initiator include but are not limited to: diacyl peroxides such as benzoyl peroxide; peroxyesters such as tert-butylperoxy benzoate; tert-butylperoxy acetate; OO-tert-butyl-O-(2-ethylhexyl)monoperoxy carbonate; peroxyketals such as n-butyl-4,4-di-(tert-butyl peroxy) valerate; and dialkyl peroxides such as 1,1-bis(tertbutylperoxy) cyclohexane; 1,1-bis(tert-butylperoxy)-3,3,5-trimethylcyclohexane; 2,2-bis(tert-butylperoxy)butane; dicumylperoxide; tert-butylcumylperoxide; Di-(2-tert-butylperoxy-isopropyl-(2)) benzene; di-tert-butylperoxide (DTBP); 2,5-dimethyl-2,5-di (tert-butylperoxy)hexane; 2,5-dimethyl-2,5-di(tert-butylperoxy)hexyne; 3,3,5,7,7-pentamethyl 1,2,4-trioxepane; and the like.

Additives

Any of the resins or layers can further include one or more additives. Suitable additives can include any one or more processing oils: (aromatic, paraffinic and napthathenic mineral oils); compatibilizers; calcined clay; kaolin clay; nanoclay; talc; silicates; carbonates; sulfates; carbon black; sand; glass beads; mineral aggregates; wollastonite; mica; glass fiber; other filler; pigments; colorants; dyes; carbon black; filler; dispersants; flame retardants; antioxidants; conductive particles; UV-inhibitors; stabilizers; light stabilizer; light absorber; coupling agents including silanes and titanates; plasticizers; lubricants; blocking agents; antiblocking agents; antistatic agents; waxes; foaming agents; nucleating agents; slip agents; acid scavengers; lubricants; adjuvants; surfactants; crystallization aids; polymeric additives; defoamers; preservatives; thickeners; rheology modifiers; humectants; coagents; vulcanizing/cross-linking/curative agents; vulcanizing/cross-linking/curative accelerators; cure retarders; and combinations thereof.

Process for Making Composite

The multilayer composite or fabric can be formed using any melt blowing process. Preferably, the multilayer composite is meltblown from an apparatus that can operate at a melt pressure from greater than 500 psi (3447 kPa) and a melt temperature within the range of 100° C. to 350° C. and capable of making fibers as fine as 1 micron in average diameter.

FIG. 1 depicts a schematic view of an illustrative meltblowing system or arrangement 100 for making the multilayer meltblown composite, according to one or more embodiments. The system 100 includes at least one extruder 110, and may include a motor 120 to maintain melt pressure within the system 100. The extruder 110 can be coupled to at least one die block or array die 130 that is coupled to a spinneret portion or spinneret 140. The die block 130 is also coupled to at least one air manifold 135 for delivering high pressure air to the spinneret portion 140 of the die block 130. The spinneret 140 includes a plurality of spinning nozzles 145 through which the melt is extruded and simultaneously attenuated with air pressure to form filaments, or fibers 150. The spinning nozzles 145 are preferably circular, die capillaries. Preferably, the spinneret 140 has a nozzle density that ranges from 20, 30, or 40 holes/inch to 200, 250, or 320 holes/inch. In one embodiment, each nozzle 145 has an inside diameter ranging of from about 0.05 mm, 0.10 mm, or 0.20 mm to 0.80 mm, 0.90 mm, or 1.00 mm.

In the die spinneret 140, the molten threads or filaments converge with a hot, high velocity, gas stream (e.g., air or nitrogen) to attenuate the filaments of molten thermoplastic material to form the individual fibers 150. The temperature and flow rate of the attenuating gas stream can be controlled using a heat exchanger 160 and air valve 170. The diameters of the filaments can be reduced by the gas stream to a desired size. Thereafter, the meltblown fibers 150 are carried by the high velocity gas stream and are deposited on a collecting surface 180 to form at least one web 185 of randomly dis-bursed meltblown fibers. The collecting surface 180 can be an exterior surface of a vacuum drum, for example.

Figure 2:
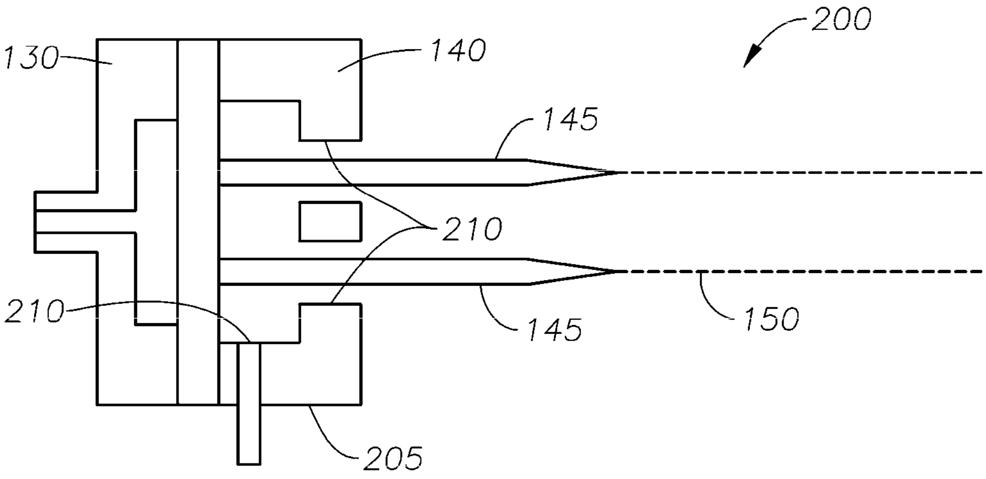
FIG. 2 depicts an enlarged schematic view of an illustrative die assembly, according to one or more embodiments described.

FIG. 2 depicts an enlarged schematic view of an illustrative die assembly 200, according to one or more embodiments. The die assembly 200 includes the die block 130 and the spinneret 140. As depicted, the air ("primary air") is provided through the primary air nozzle 210 located at least on a side of the die spinneret 140. The die block 130 can be heated using the primary air, a resistive heating element, or other known device or technique (not shown), to prevent the die block 130 from becoming clogged with solidifying polymer as the molten polymer exits and cools. The air also draws, or attenuates, the melt into fibers. Secondary, or quenching, air at temperatures above ambient can also be provided through the die block 130. Primary air flow rates typically range from about 1 to 30 standard cubic feet per minute per inch of die width (SCFM/inch). In certain embodiments, the primary air pressure in the meltblown process typically ranges from a low of about 2 psig, 3, psig, 5 psig, or 7 psig to about 10 psig, 15 psig, 20 psig, or 30 psig at a point in the die block 130 just prior to exit. Primary air temperatures are typically within the range from 150° C., 200° C., or 230° C. to 300° C., 320° C., or 350° C.

The melting temperature (Tm) of the resins can range from 50° C. to 300° C. In yet other embodiments, the melting temperature is at least 50° C. and less than 150° C., 200° C., 220° C., 230° C., 250° C., 260° C., 270° C., 280° C., 290° C., 300° C., 310° C., or 320° C. The resin can be formed into fibers at a melt pressure from greater than 500 psi (3447 kPa) or 750 psi (5171 kPa) or 1,000 psi (6895 kPa) or 2,000 psi (13790 kPa), or within the range from 500 psi (3447 kPa) or 750 psi (5171 kPa) to 1,000 psi (6895 kPa) or 2,000 psi (13790 kPa) or 2,500 psi (17237 kPa).

Expressed in terms of the amount of composition flowing per inch of the die per unit of time, throughputs for the manufacture of meltblown fabrics using the compositions described herein are typically within the range from 0.1, 0.2, 0.3, or 0.5 to 1.0, 1.5, 2.0, or 3.0 grams per hole per minute (ghm). Thus, for a die having 30 holes per inch, polymer throughput is typically about 0.25, 0.5, or 1.0 to about 4, 8, or 12 lbs/inch/hour (PIH).

Because such high temperatures can be used, a substantial amount of heat is desirably removed from the fibers in order to quench, or solidify, the fibers leaving the nozzles. Although not shown, cold gases of air or nitrogen can be used to accelerate cooling and solidification of the meltblown fibers. In particular, cooling ("secondary") air flowing in a cross-flow direction (perpendicular or angled) relative to the direction of fiber elongation may be used to quench meltblown fibers. Also, an additional, cooler pressurized quench air may be used and can result in even faster cooling and solidification of the fibers. In certain embodiments, the secondary cold air flow may be used to attenuate the fibers. Through the control of air and array die temperatures, air pressure, and polymer feed rate, the diameter of the fiber formed during the meltblown process may be regulated.

Figure 3:
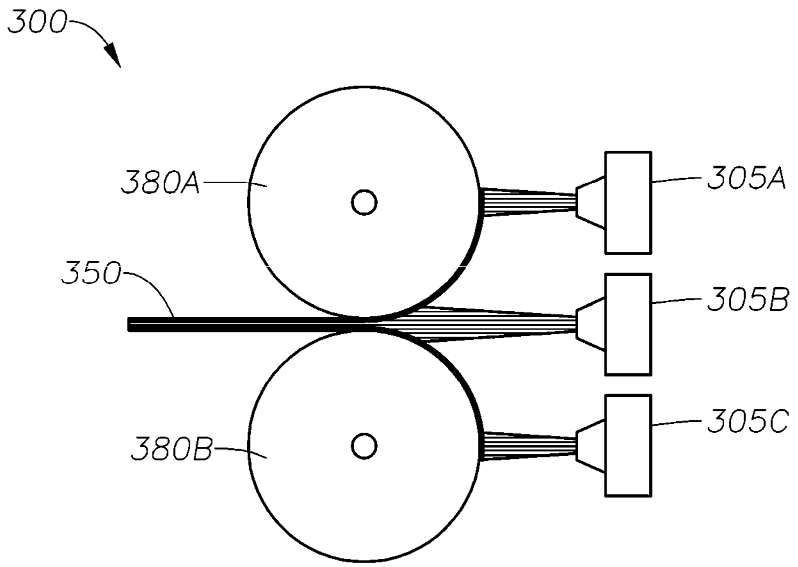
FIG. 3 depicts a schematic of an illustrative meltblowing system for making a multilayer meltblown composite, according to one or more embodiments described. As depicted, the dies and collection surfaces can be vertically disposed.

FIGS. 3 through 8 depict schematics of various illustrative meltblowing systems or arrangements that can be used to make the multi-layered composites described herein. FIG. 3, for example, depicts a schematic of an illustrative meltblowing system 300 for making a multilayer meltblown composite 350. The meltblowing system 300 can include three or more vertically arranged dies 305A, 305B, 305C. Each die 305A, 305B, 305C can be similar to the die 200 discussed and described above with reference to FIG. 2. Any resin or combination of resins can be blown through any given die 305A, 305B, 305C, where the first die 305A provides a first facing or first outer layer, the second die 305B provides a core layer or intermediate layer, and the third die 305C provides a second facing layer or second outer layer.

The meltblowing system 300 can further include two or more collection surfaces 380A, 380B that are vertically aligned. Each collection surface 380A, 380B can be similar to the collection drum 180 depicted and described above with reference to FIG. 1. The collection surfaces 380A, 380B can be adjacent one another such that a desired gap ("nip") is defined therebetween. As depicted, fibers from each die 305A, 305B, 305C are horizontally directed toward and collected on the collection surfaces 380A and/or 380B to form a three layer fabric composite 350. The dies 305A, 305B, 305C can be independently movable with respect to one another. The dies 305A, 305B, 305C can also be independently movable with respect to the collection surfaces 380A, 380B to vary the die to collector distance ("DCD").

Figure 4:
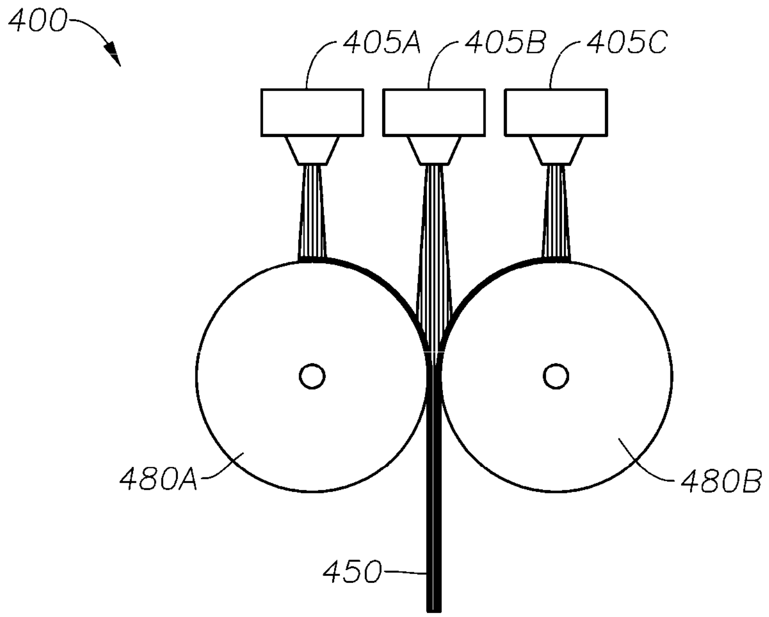
FIG. 4 depicts a schematic of another illustrative meltblowing system for making a multilayer meltblown composite, according to one or more embodiments described. As depicted, the dies and collection surfaces can be horizontally disposed.

FIG. 4 depicts a schematic of another illustrative meltblowing system 400 for making a multilayer meltblown composite 450, according to one or more embodiments. The meltblowing system 400 can include three or more horizontally arranged dies 405A, 405B, 405C and horizontally aligned collection surfaces 480A, 480B. Each die 405A, 405B, 405C can be similar to the die 200 discussed and described above with reference to FIG. 2. Each collection surface 480A, 480B can be similar to the collection drum 180, as depicted and described above with reference to FIG. 1. The dies 405A, 405B, 405C can be independently movable with respect to one another. The dies 405A, 405B, 405C can also be independently movable with respect to the collection surfaces 480A, 480B to vary the DCD.

Any resin or combination of resins can be vertically extruded through any given die 405A, 405B, 405C to provide a multi-layer composite having first and second facing layers disposed about a core layer, as described herein. As depicted, fibers from each die 405A, 405B, 405C are directed toward and collected on the collection surfaces 480A and/or 480B to form a three layer fabric composite 450.

Figure 5:
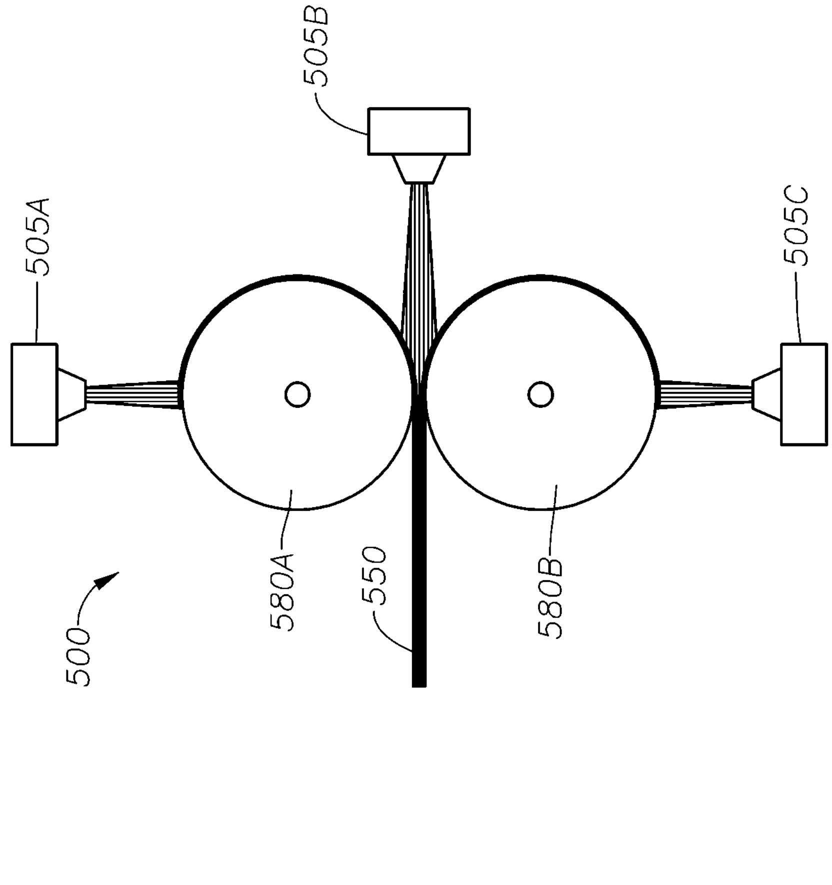
FIG. 5 depicts a schematic of another illustrative meltblowing system for making a multilayer meltblown composite, according to one or more embodiments described. As depicted, the collection surfaces can be vertically disposed and the dies can be arranged anywhere about the collection surfaces.

FIG. 5 depicts a schematic of another illustrative meltblowing system 500 for making a multilayer meltblown composite 550, according to one or more embodiments. The meltblowing system 500 can include three or more dies 505A, 505B, 505C to provide a multi-layer composite having first and second facing layers disposed about a core layer, as described herein. Each die 505A, 505B, 505C can be similar to the die 200 discussed and described above with reference to FIG. 2. The meltblowing system 500 can further include two or more collection surfaces 580A, 580B that are vertically aligned. Each collection surface 580A, 580B can be similar to the collection drum 180, as depicted and described above with reference to FIG. 1.

The first die 505A and the third die 505C can be vertically aligned with respect to one another and located on opposing sides of the collection surfaces 580A, 580B. The second die 505B can be located intermediate the first and third dies 505A, 505C or provide a three layer fabric composite 550.

Any resin or combination of resins can be extruded through any given die 505A, 505B, 505C to provide the multi-layer composite 550. The dies 505A, 505B, 505C can be independently movable with respect to one another. The dies 505A, 505B, 505C can also be independently movable with respect to the collection surfaces 580A, 580B to vary the DCD.

Figure 6:
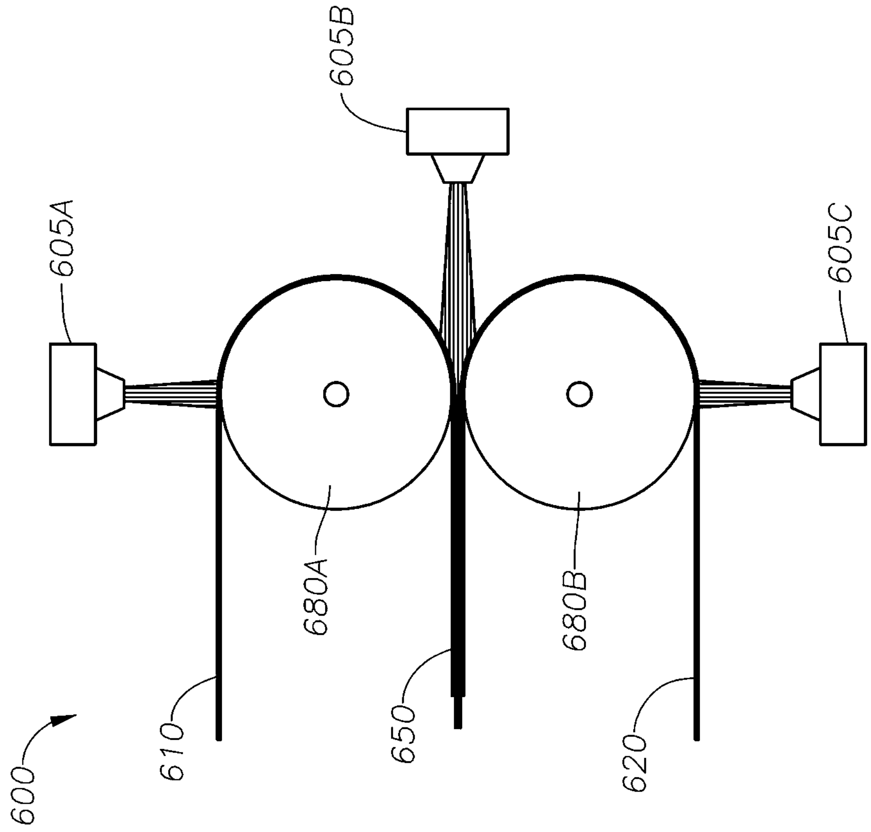
FIG. 6 depicts a schematic of yet another illustrative meltblowing system for making a multilayer meltblown composite, according to one or more embodiments described. As depicted, the collection surfaces can be vertically disposed and the dies can be arranged anywhere about the collection surfaces. One or more facing layers can also be introduced to collection surfaces and fibers meltblown thereon.

FIG. 6 depicts a schematic of yet another illustrative meltblowing system 600 for making a multilayer meltblown composite 650, according to one or more embodiments. The meltblowing system 600 can include three or more dies 605A, 605B, 605C. Each die 605A, 605B, 605C can be similar to the die 200 discussed and described above with reference to FIG. 2. The meltblowing system 600 can further include two or more collection surfaces 680A, 680B that are vertically aligned. Each collection surface can be similar to the collection drum 180, as depicted and described above with reference to FIG. 1. Like the embodiment of FIG. 5, the first die 605A and the third die 605C can be vertically aligned with respect to one another and located on opposing sides of the collection surfaces 680A, 680B while the second die 605B can be located intermediate the first and third dies 605A, 605C.

A first facing layer 610 can be introduced to the meltblowing system 600 via the first collection surface 680A. A second facing layer 620 can also be introduced to the meltblowing system 600 via the second collection surface 680B. As shown, the collection surfaces 680A, 680B provide facing layers 610, 620, respectively, on which the fibers blown from the dies 605A, 605B, 605C, respectively, are collected. Accordingly, the resulting multilayer composite has at least five layers.

Any resin or combination of resins can be extruded through any given die 605A, 605B, 605C. The dies 605A, 605B, 605C can be independently movable with respect to one another. The dies 605A, 605B, 605C can also be independently movable with respect to the collection surfaces 180A, 180B and/or the facing layers 610, 620 disposed on the collection surfaces 180A, 180B.

Figure 7:
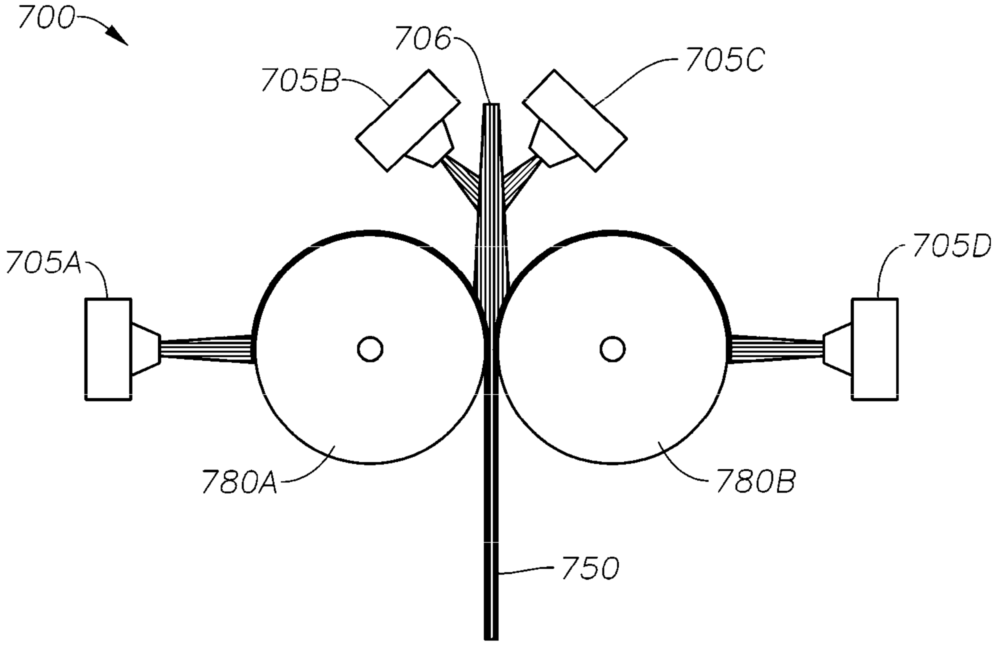
FIG. 7 depicts a schematic of still another illustrative meltblowing system for making a multilayer meltblown composite, according to one or more embodiments described. As depicted, the collection surfaces can be horizontally disposed and the dies can be arranged anywhere about the collection surfaces. Two or more dies can also be used to form the intermediate or core layer.

FIG. 7 depicts a schematic of still another illustrative meltblowing system 700, according to one or more embodiments. The meltblowing system 700 can include four or more dies 705A, 705B, 705C, 705D. Each die 705A, 705B, 705C, 705D can be similar to the die 200 discussed and described above with reference to FIG. 2. The meltblowing system 700 can further include two or more collection surfaces 780A, 780B that are horizontally aligned. Each collection surface 780A, 780B can be similar to the collection drum 180, as depicted and described above with reference to FIG. 1.

At least two dies, such as die 705A and die 705D, can be horizontally aligned with respect to one another and located on opposing sides of the collection surfaces 780A, 780B. And at least two dies, such as die 705B and die 705C, can be located intermediate the dies 705A, 705D. The dies 705A, 705B, 705C, 705D can be independently movable with respect to one another. The dies 705A, 705B, 705C, 705D can also be independently movable with respect to the collection surfaces 180A, 180B to vary the DCD.

Any resin or combination of resins can be extruded through any given die 705A, 705B, 705C, 705D to provide the multilayer composite 750. As depicted, fibers from each die 705A, 705B, 705C, 705D are directed toward and collected on the collection surfaces 780A, 780B to form a three layer fabric composite 750. The middle or intermediate layer, i.e., "core" layer, can include a mixture of fibers produced from dies 705B, 705C. An additional layer of resin or one or more additives can be sprayed or otherwise introduced through nozzle 706 located between dies 705B and 705C.

Figure 8:
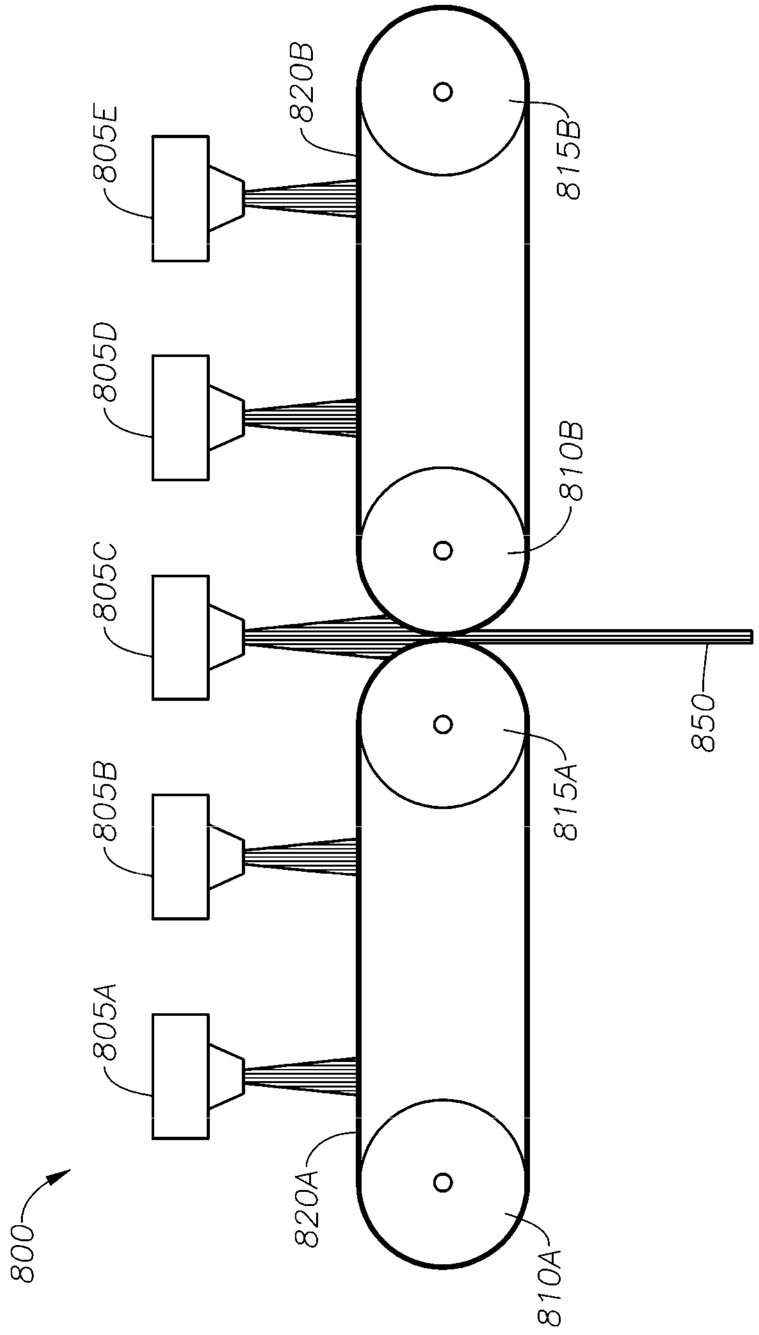
FIG. 8 depicts a schematic of yet another illustrative meltblowing system for making a multilayer meltblown composite, according to one or more embodiments described. As depicted, the collection surfaces can be horizontal belts or conveyors, and the dies can be arranged anywhere about the collection surfaces.

FIG. 8 depicts a schematic of yet another illustrative meltblowing system 800, according to one or more embodiments. The meltblowing system 800 can include five or more dies 805A, 805B, 805C, 805D, 805E. Each die 805A, 805B, 805C, 805D, 805E can be similar to the die 200 discussed and described above with reference to FIG. 2. The meltblowing system 800 can further include two or more horizontally arranged collection surfaces 820A, 820B. As depicted, a first collection surface 820A can be a conveyor belt disposed about and moved by two horizontally aligned drums 810A and 815A. Similarly, a second collection surface 820B can be a conveyor belt disposed about and moved by two horizontally aligned drums 810B, 815B. The collection surfaces 820A, 820B can be adjacent one another such that a desired gap ("nip") is defined therebetween.

Each die 805A, 805B, 805C, 805D, 805E can be horizontally aligned above the collection surfaces 820A, 820B or aligned in other spatial orientation. The dies 805A, 805B, 805C, 805D, 805E can be independently movable with respect to one another. The dies 805A, 805B, 805C, 805D, 805E can also be independently movable with respect to the collection surfaces 820A, 820B.

The collection surfaces 820A, 820B can provide a collection surface for fibers produced from the dies 805A, 805B, 805C, 805D, 805E. Any resin or combination of resins can be extruded through any given die 805A, 805B, 805C, 805D, 805E. As depicted, fibers from each die 805A, 805B, 805C, 805D, 805E are directed toward and collected on the collection surfaces 820A and/or 820B to form a five layer fabric composite 850.

Figure 9:
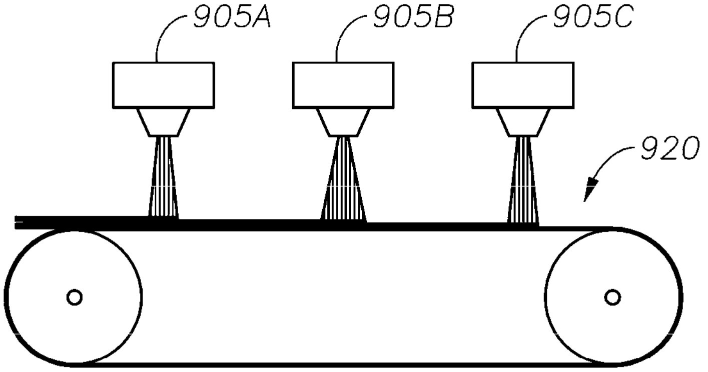
FIG. 9 depicts a schematic of still yet another illustrative meltblowing system for making a multilayer meltblown composite, according to one or more embodiments described. As depicted, a single collection surface can be used, and the dies can be arranged anywhere about the collection surfaces.

FIG. 9 depicts a schematic of still yet another illustrative meltblowing system 900 for making a multilayer meltblown composite, according to one or more embodiments described. As depicted, a single collection surface 920 can be used, and the dies 905A, 905B, 905C can be arranged anywhere about the collection surfaces.

Referring to any system or arrangement described above 100, 200, 300, 400, 500, 600, 700, 800, or 900 with regard to FIGS. 1 through 9 or elsewhere herein, the laminate may be passed through the nip between the unheated or heated smooth collection surface(s), or unheated or heated patterned collection surface(s), or a combination of two or more of these, while applying light pressure thereon, as another extensible construction is contacted with the laminate to form a multilayer construction. Given the formation of the multilayer constructions as described herein, in certain embodiments, adhesives are substantially absent from the constructions, meaning that adhesives are not used to secure the layers of fabric and/or film to one another. As used herein, an "adhesive" is a substance that is used to secure two layers of film or fabric to one another as is known in the art. Examples of adhesive substances include polyolefins, polyvinyl acetate polyamides, hydrocarbon resins, waxes, natural asphalts, styrenic rubbers, and blends thereof. Also, in each configuration 300, 400, 500, 600, 700, and 800 described, the innermost layer ("core layer") can be blown symmetrically with respect to the nip of the collection surface(s), as depicted in FIGS. 3-8, and although not shown, the innermost layer ("core layer") in each configuration 300, 400, 500, 600, 700, and 800 described can be blown asymmetrically with respect to the nip of the collection surface(s).

In one or more embodiments above or elsewhere herein, the meltblown fibers may be continuous or discontinuous and are generally within the range from 0.5 to 250 microns in average diameter, preferably less than 200 microns, less than 150 microns, less than 100 microns, less than 75 microns, less than 50 microns, less than 40 microns, less than 30 microns, less than 20 microns, less than 10 microns, less than 5 microns, less than 4 microns, less than 3 microns, less than 2 microns, or less than 1 microns. In certain embodiments, the meltblown fibers can have a diameter within the range of from 5 or 6 or 8 or 10 to 20 or 50 or 80 or 100 or 150 or 200 or 250 μm in average diameter, and in other embodiments have a diameter from less than 80 or 50 or 40 or 30 or 20 or 10 or 5 μm.

In one or more embodiments above or elsewhere herein, the fiber diameters of each layer of the multi-layered composite can be the same or different. Accordingly, a ratio of fiber diameters of adjacent layers can be the same or vary. For example, a ratio of fibers diameters of adjacent layers can range from a low of about 0.1:1 to a high of about 1:200. Such ratios can also range from about 1:150; 1:100; 1:75; 1:50; 1:25; 1:10; 1:5; or 1:2.

In one or more embodiments above or elsewhere herein, at least 1% of the fibers in any given layer of the multi-layered structure can be co joined or married. More preferably, at least 2%, 5%, 10%, 15%, 20%, or 25% of the fibers in any given layer of the multi-layered structure can be co joined or married. The amount of co joined or married fibers can also range from a low of about 1%, 5%, or 10% to a high of about 25%, 35%, or 45%.

In one or more embodiments above or elsewhere herein, the fibers of any one or more layers of the multi-layered structure can exhibit or possess some extent of fusion, melting, entrainment or mechanical interlocking with the fibers of any one or more adjoining layers without a sharp delineated interface between layers.

In one or more embodiments above or elsewhere herein, at least one layer of the multi-layered structure can recover at least 80% of it original length after 100% extension and at least 70% of it original length after 200% extension. In one or more embodiments, the multi-layered structure can recover at least 80% of it original length after 100% extension and at least 70% of it original length after 200% extension.

In one or more embodiments above or elsewhere herein, the force at 50% extension of at least one layer of the multi-layered structure, upon elongating the sample to 100% of its original length and then upon unloading, is about $1.3\times10^{-3}$ lbf/in/gsm.

In one or more embodiments above or elsewhere herein, the multi-layered structure has a hydrohead of about 0.05 mbar/gsm or more. Preferably, the hydrohead is greater than 0.1 mbar/gsm, 0.2 mbar/gsm, 0.3 mbar/gsm, 0.4 mbar/gsm, or 0.5 mbar/gsm. The hydrohead can also range from a low of about 0.1 mbar/gsm, 0.2 mbar/gsm or 0.3 mbar/gsm to a high of about 0.7 mbar/gsm, 0.8 mbar/gsm, or 0.9 mbar/gsm.

In one or more embodiments above or elsewhere herein, the air permeability of any one or more layers of the multi-layered structure is about 0.02 $cm^3/cm^2/s$ or more. In one or more embodiments, the air permeability of the multi-layered structure is about 0.02 $cm^3/cm^2/s$ or more. The air permeability can also range from a low of about 0.02 $cm^3/cm^2/s$, 0.05 $cm^3/cm^2/s$, or 1.0 $cm^3/cm^2/s$ to a high of about 2.0 $cm^3/cm^2/s$, 3.0 $cm^3/cm^2/s$ or 5.0 $cm^3/cm^2/s$.

In one or more embodiments above or elsewhere herein, the fabrics may have a basis weight within the range of from 10 or 20 or 30 to 50 or 80 or 100 or 150 $g/m^2$. These fabrics may also be characterized by having an Ultimate Elongation from greater than 200% or 300% or 500% or 1,000%. In this manner, multilayer constructions can be formed having at least three melt-blown layers ("MMM"). Other multi-layered meltblown structures are contemplated such as $M_xQ$, $QM_xQ$, $M_x$, $QM_x$, $Q_xS$, $M_xA_yM_y$, $QM_xA_yM_yQ$, $QM_xQM_yS$, $QM_x$-$QM_y$, $M_xQM_yQ$, $QQM_xQ$, where x is at least 3 and y is 0 to 100. For example, x can be 3 to 100; 3 to 50; 3 to 25; or 3 to 10; x can also range from a low of about 3, 4, or 5 to a high of about 6, 10, or 15; x can also range from a low of about 1, 2, 3, 4, or 5 to a high of about 6, 7, 8, 10, or 15. "M" represents a layer of meltblown fabric (where each "M" in a construction may be the same or different); "Q" represents a spunbond, spunlace, woven fabric, or film (where each "S" in a construction may be the same or different), and "A" represents one or more additives. When adhering of the meltblown fibers to another fabric is desired, the secondary cooling air flow may be diminished and/or heated to maintain some of the melt quality and hence bonding ability of the forming elastic meltblown fibers to the fabrics upon which they are bonded.

More particularly, in forming a multilayered construction, the polyolefin polymers may be meltblown onto an extensible fabric, such as a spunlace fabric, that is passed underneath or in front of the forming meltblown fabric. The melt temperature and distance between the spinnerets and the passing extensible fabric is adjusted such that the fibers are still in a melt or partial melt state when contacting the fabric(s) to form a two or three layer construction. The coated fabric(s) then has the melted or partially-melted elastic meltblown fibers/fabric adhered thereto.

Fiber

The fiber can be a single component fiber. The fiber can also be a multi-component fiber formed from a process wherein at least two polymers are extruded from separate extruders and melt-blown or spun together to form one fiber. In one or more embodiments, the polymers used in the multi-component fiber are the same or substantially the same. In one or more embodiments, the polymers used in the multi-component fiber are different from each other. The configuration of the multi-component fiber can be, for example, a sheath/core arrangement, a side-by-side arrangement, a pie arrangement, an islands-in-the-sea arrangement, or a variation thereof. The fiber can also be drawn to enhance mechanical properties via orientation, and subsequently annealed at elevated temperatures, but below the crystalline melting point to reduce shrinkage and improve dimensional stability at elevated temperature.

In certain embodiments, where a separate fabric or layer is unwound into the process, such as FIG. 6 for example, and is for example used as a facing layer for the laminate, these fabrics can be continuous fibers such as found in spunbonded fabrics, staple fibers, or discontinuous fibers, such as those found in carded fabrics. The length and diameter of the staple fibers can vary depending on the desired toughness and stiffness of the fiber reinforced composition. In one or more embodiments, the fibers have a length of ¼ inch, or a length within the range having a lower limit of ⅛ inch (0.3175 cm), or ⅙ inch (0.423 cm), and an upper limit of 1 inch (2.54 cm), or 1.5 inch (3.81 cm) or 5 inch (12.70 cm). In one or more embodiments, the diameter of the fibers is within the range having a lower limit of 0.1 microns and an upper limit of 100 microns. The diameters can also range from a low of 0.1 microns, 0.5 microns, or 1.0 microns to a high of about 5 microns, 10 microns or 15 microns. Suitable ranges also include 0.1 to 8 microns; 0.2 to 7 microns; 0.3 to 6 microns, 0.1 to 5 microns; and 0.1 to 3 microns.

In certain embodiments, the mechanical properties of the meltblown fabrics (or multilayer constructions) described herein can be enhanced by a stretching or orientation process. Annealing can be combined with mechanical orientation, in either or both the CD or the MD. If desired, mechanical orientation can be done by the temporary, forced extension of the fabric for a short period of time before it is allowed to relax in the absence of the extensional forces. In the meltblowing process, there may be some degree of orientation of the fibers in the MD imparted due to the laydown or spinning process alone. But in certain embodiments, no additional mechanical orientation or stretching is needed. Thus, in certain embodiments, the meltblown fabrics described herein have a low degree of, or no, orientation. In other embodiments, orientation is imparted in the CD but not the MD. Thus, in certain embodiments the meltblown fabric possesses an MD Elongation less than 20 or 50 or 80 or 100% and a CD Elongation greater than 100 or 200 or 300%. Stated another way, the meltblown fabric possesses a CD/MD elongation at break ratio of between 0.1 or 0.5 and 2 or 3 or 5 or 7 or 10.

In one embodiment, the formation of the elastic fibers and fabrics includes an annealing step with or without mechanical orientation. Annealing may also be done after fabrication of the fabric from the elastic fibers. In certain embodiments, the elastic meltblown fiber or fabric is annealed at a temperature within the range from 50° C. or 60° C. to 130° C. or 160° C. Thermal annealing of the fabric is conducted by maintaining the fabric at a temperature within the range above for a period from 1 second to 1 minute, preferably between 1 and 10 seconds. The annealing time and temperature can be adjusted for any particular copolymer or copolymer composition. In another embodiment, the meltblown fabrics can be annealed in a single-step by a heated roll during calendaring under low tension. In other embodiments, the meltblown fabrics require little to no post fabrication processing.

In certain embodiments, the forming multilayer construction is further processed by passing the multilayer construction through a hydroentangling apparatus, thus further bonding the web of elastic fibers to each other or other adjacent fabric layers by interlocking and entangling the fibers about each other with high velocity streams of water. Hydroentangling is known in the art and described in some detail by A.M. Seyam et al., "An Examination of the Hydroentangling Process Variables," in INT'L NONWOVENS J. pp. 25-33 (Spring 2005).

As mentioned above, the fibers can be continuous (long fibers) or discontinuous (short fibers). Long fibers will have a length to diameter aspect ratio greater than 60, preferably 200 to 500; and the short fibers will have a length to diameter aspect ratio less than 60, preferably 20 to 60. The number of fibers per square inch (fiber density) of the meltblown fabric preferably ranges from a low of 20 fibers/in$^2$, 40 fibers/in$^2$, or 50 fibers/in$^2$ to a high of 100 fibers/in$^2$, 250 fibers/in$^2$, or 500 fibers/in$^2$. Suitable ranges also include: 25 fibers/in$^2$ to 400 fibers/in$^2$; 50 fibers/in$^2$ to 300 fibers/in$^2$; 60 fibers/in$^2$ to 200 fibers/in$^2$; 20 fibers/in$^2$ to 80 fibers/in$^2$; and 30 fibers/in$^2$ to 70 fibers/in$^2$.

The multilayered construction can be mechanically stretched to tailor the elastic performance of the composite. Not wishing to be bound by theory, it is believed that initial stretching modifies the structure of the elastomeric components in the composite, and potentially the interfacial bonding among fibers between and/or within layers. An initial stretching can reduce the hysteresis loop, which is a measure of the energy absorbed by the elastomer during deformation. An ideal elastomer has no hysteresis, or put another way, all the energy put into the elastomer, or stored in the elastomers, is given back upon returning the elastomer to its original size and shape. There are few elastomers and even fewer elastic laminates that show ideal elastic behavior. Most if not all show some level of hysteresis. An initial loading and unloading cycle will typically reduce the hysteresis loop which means that the material or laminate is a more efficient elastomer. The mechanical stretching of elastomers and elastomeric composites can have other advantageous effects, such as reducing the peak load at deformation, potentially improved permanent set, retractive force, and adjusting the aesthetics of the outer layers/surfaces.

There are many different methods for mechanically stretching a composite in both machine direction (MD) and cross-direction (CD). Devices based upon intermeshing blades or disks are effective at incrementally stretching fabrics in either MD or CD, respectively, or both when units are placed in series. The term incremental stretching arises from the fact the fabrics are stretched in an incremental fashion across their entire width or length. The increment or distance over which the fabric is stretched is determined by the spacing of adjacent disks or blades and the distance of interpenetration between the two sets of disks or blades. Examples of this and similar technology using grooved rolls rather than separate disks can be found in U.S. Pat. Nos. 4,223,059; 4,251,585; 4,285,100; and 4,368,565. Further improvements to this basic technology allowing narrower webs/films to be efficiently stretched, or to increase the amount of stretching or vary the amount of stretch across a web can be found in U.S. Pat. Nos. 5,143,679; 5,156,793; and 5,167,897.

Other technologies are available for stretching webs that are better suited for MD stretching. An example of using nip rolls for this purpose is described in U.S. Pat. No. 7,320,948 in which sets of two nip rolls running at different speeds enable fabrics and laminates to be stretched in MD.

Specific Layer Blends

In one or more preferred embodiments, at least one layer of the multilayer composite includes at least one propylene-based or ethylene-based homopolymers or random, block, or graft copolymers comprising none (i.e., homopolymers) or from 0.1 wt % or 1 wt % or 2 wt % or 5 wt % to 10 wt % or 15 wt % or 20 wt % or 45 wt % of the polymer, of comonomer-derived units selected from ethylene and C4-C10 α-olefins (propylene-based polymers) and $C_3$-$C_{10}$ α-olefins (ethylene-based polymers). Preferably, at least one layer of the multilayer composite includes one or more polypropylenes within the range of from about 50 wt % to 99 wt %; or 60 wt % to 95 wt %; or 50 wt % to 90 wt %; or 55 wt % to 85 wt %, by weight of the fabric layer/composition. In one or more embodiments, at least one layer of the multilayer composite consists essentially of one or more polypropylenes.

In one or more embodiments, the core layer includes a blend of at least one propylene-α-olefin copolymer resin and at least one polypropylene resin. For example, a preferred blend includes 50 wt % of one or more propylene-α-olefin copolymer resins and 50 wt % of one or more polypropylene resins. The amount of the propylene-α-olefin copolymer resin in the blend can range from a low of about 20 wt %, 30 wt %, or 40 wt % to a high of about 60 wt %, 70 wt %, or 90 wt %. The amount of the polypropylene resin in the blend can range from a low of about 1 wt %, 5 wt %, or 10 wt % to a high of about 20 wt %, 30 wt %, or 45 wt %.

In one or more preferred embodiments, at least one facing layer includes a blend of polypropylene and less than 50 wt % of one or more blend components. The blend component can be one or more impact copolymers, one or more random copolymers (RCP), one or more polyethylenes, one or more polyethylenes having a Mw of less than 20,000 g/mol, one or more polypropylenes having a Mw of less than 20,000 g/mol, one or more polyalphaolefins, or any combination(s) thereof. The amount of the blend component (not the polypropylene) can be present in an amount ranging from a low of about 0.5 wt %, 1 wt %, or 5 wt % to a high of about 30 wt %, 40 wt %, or 50 wt %. For example, the amount of the blend component can be of from about 1 wt % to 49 wt %; or about 5 wt % to 45 wt %; or about 5 wt % to 40 wt %; or about 5 wt % to 25 wt %.

The MFR (ASTM D1238, 230° C., 2.16 kg) of the facing layer resin or blend is preferably less than 2,000 dg/min (g/10 min), more preferably 1,500 dg/min or less, 1,200 dg/min or less, 900 dg/min or less, 600 dg/min or less, 300 dg/min or less, 200 dg/min or less, 150 dg/min or less, 100 dg/min or less, or 90 dg/min or less. In certain embodiments, the MFR of the extensible resin or blend can range from a low of about 50 dg/min, 75 dg/min, or 80 dg/min to a high of about 250 dg/min, 500 dg/min, or 1,000 dg/min. The MFR of the facing layer resin or blend can also range from a low of about 20 dg/min, 30 dg/min, or 40 dg/min to a high of about 90 dg/min, 120 dg/min, or 150 dg/min. The MFR of the facing layer resin or blend can also range from a low of about 20 dg/min, 35 dg/min, or 45 dg/min to a high of about 65 dg/min, 80 dg/min, or 95 dg/min. The MFR of the facing layer resin or blend can further range from a low of about 0.1 dg/min, 0.5 dg/min, 1 dg/min, or 5 dg/min to a high of about 30 dg/min, 40 dg/min, 70 dg/min, or 90 dg/min.

The weight average molecular weight (Mw) of the facing layer resin or blend is preferably less than 500,000; 400,000; 300,000; or 250,000. For example, the Mw of the facing layer resin or blend can range from about 50,000 to about 200,000. In one or more embodiments, the Mw of the facing layer resin or blend can range from a low of about 50,000; 80,000; or 100,000 to a high of about 155,000; 170,000; or 190,000. In one or more embodiments, the Mw of the facing layer resin or blend can range from about 80,000 to about 200,000; 100,000 to about 175,000; or 140,000 to about 180,000.

The MFR (ASTM D1238, 230° C., 2.16 kg) of the core layer resin or blend is preferably less than 2,000 dg/min (g/10 min); more preferably 1,500 dg/min or less; 1,200 dg/min or less; 900 dg/min or less; 600 dg/min or less; 300 dg/min or less; 200 dg/min or less; 150 dg/min or less; 100 dg/min or less; or 90 dg/min or less. In certain embodiments, the MFR of the core layer resin or blend can range from a low of about 50 dg/min; 75 dg/min; or 80 dg/min; to a high of about 250 dg/min; 500 dg/min; or 1,000 dg/min. The MFR of the core layer resin or blend can also range from a low of about 20 dg/min; 30 dg/min; or 40 dg/min; to a high of about 90 dg/min; 120 dg/min; or 150 dg/min. The MFR of the core layer resin or blend can also range from a low of about 25 dg/min; 35 dg/min; or 45 dg/min; to a high of about 75 dg/min; 85 dg/min; or 95 dg/min. The MFR of the core layer resin or blend can further range from a low of about 0.1 dg/min; 0.5 dg/min; 1 dg/min; or 5 dg/min; to a high of about 30 dg/min; 40 dg/min; 70 dg/min; or 90 dg/min. In at least one specific embodiment, the MFR of the core layer resin or blend ranges from about 2 dg/min to about 90 dg/min; about 2 dg/min to about 20 dg/min; about 3 dg/min to about 90 dg/min; or about 3 dg/min to about 20 dg/min.

The Mw of the core layer resin or blend is preferably less than 500,000; 400,000; 300,000; or 250,000. For example, the Mw of the core layer resin or blend can range from about 50,000 to about 290,000. In one or more embodiments, the Mw of the core layer resin or blend can range from a low of about 50,000; 65,000; or 80,000; to a high of about 130,000; 190,000; or 290,000. In one or more embodiments, the Mw of the core layer resin or blend can range from about 80,000 to about 285,000; 80,000 to about 240,000; or 80,000 to about 140,000.

One method of characterizing multilayer construct elasticity is to determine a hysteresis curve according to the following cyclic testing procedure. Generally, a sample of nonwoven fabric is stretched one or more times using an Instron 1130 instrument, which is commercially available from Instron Corporation. Unless stated otherwise, the test parameters used herein to generate hysteresis curves are: sample width=1 inch, sample length=3 inches, gauge length, i.e., distance between clamps, is 1 inch, crosshead speed, i.e., speed of top clamp that is applying a stretching force, is 10 in/min. As used herein "first cycle" and "second cycle" refer to the number of times an individual sample has been stretched.

Samples are tested by first cutting a nonwoven fabric sample to the specified sample size. Each test sample is loaded in to an Instron 1130 instrument by first attaching the sample to the crosshead/top clamp and then to the bottom clamp. The distance between the clamps is the specified gauge length. No pre tension is applied on the sample.

The sample is then stretched to the desired strain, e.g., 100%, or 200%, as measured by sample length, using a crosshead speed, i.e., stretch speed, of 10 in/min. The sample is then returned to zero load at the same crosshead speed without any hold time. The force on the sample as a function of strain during extension and retraction is recorded.

The sample is removed from the instrument for further characterization or stretched one or more times if additional cycle data was desired, e.g., second cycle data. Second cycle hysteresis curves are prepared by remounting samples already tested in a first cycle. Samples are mounted using the same gauge length unless specifically reported otherwise. The same procedure described above for the first cycle is utilized for the second cycle.

Unless described otherwise herein, permanent set is the amount of strain remaining in a sample after retraction from a specified strain expressed as a percentage of the specified strain. The elongation remaining in the sample at zero load after retraction (as determined by the intercept of the retraction curve with the x-axis) is divided by the maximum elongation the sample was stretched during that cycle.

Unless described otherwise herein, retractive force at 50% is the force exerted by a sample after stretching to a given elongation and allowing the sample to retract to one-half of that elongation.

Unless described otherwise herein, peak load (lbs/in) is the maximum load in pounds force exerted on the sample during extension divided by the width of the sample in inches.

Unless described otherwise herein, peak force MD (N) is the maximum force exerted on a sample during extension in the machine direction (MD) expressed in Newtons.

Unless described otherwise herein, peak force CD (N) is the maximum force exerted on a sample during extension in the cross direction (CD) expressed in Newtons.

Unless described otherwise herein, elongation at break MD (%) is the increase in length of a sample measured at the breaking point after extension in the machine direction divided by the original gauge length expressed as a percentage.

Unless described otherwise herein, elongation at break CD (%) is the increase in length of a sample measured at its breaking point after stretching in the cross direction divided by the original gauge length expressed as a percentage.

Co-Agents

The resin or resin blends can optionally include one or more co-agents. Suitable co-agents can include liquid and metallic multifunctional acrylates and methacrylates, functionalized polybutadiene resins, functionalized cyanurate, and allyl isocyanurate. More particularly, suitable co-agents can include, but are not limited to polyfunctional vinyl or allyl compounds such as, for example, triallyl cyanurate, triallyl isocyanurate, pentaerthritol tetramethacrylate, ethylene glycol dimethacrylate, diallyl maleate, dipropargyl maleate, dipropargyl monoallyl cyanurate, azobisisobutyronitrile, and the like, and combinations thereof. Commercially available co-agents can be purchased from Sartomer.

In one or more embodiments, the resin or resin blends contain at least 0.1 wt % of co-agent based on the total weight of blend. In one or more embodiments, the amount of co-agent(s) can range from about 0.1 wt % to about 15 wt %, based on the total weight of blend. In one or more embodiments, the amount of co-agent(s) can range from a low of about 0.1 wt %, 1.5 wt % or 3.0 wt % to a high of about 4.0 wt %, 7.0 wt %, or 15 wt %, based on the total weight of blend. In one or more embodiments, the amount of co-agent(s) can range from a low of about 2.0 wt %, 3.0 wt % or 5.0 wt % to a high of about 7.0 wt %, 9.5 wt %, or 12.5 wt %, based on the total weight of blend. In one or more embodiments, the amount of co-agent(s) is about 3 wt %, based on the total weight of blend.

Antioxidants

The resin or resin blends can optionally include one or more anti-oxidants. Suitable anti-oxidants can include: hindered phenols; phosphites; hindered amines; Irgafos 168; Irganox 1010; Irganox 3790; Irganox B225; Irganxo 1035; Irgafos 126; Irgastab 410; Chimassorb 944, etc., made by Ciba Geigy Corp. These may be added to the resin or resin blends to protect against degradation during shaping or fabrication operation and/or to better control the extent of chain degradation.

In one or more embodiments, the resin or resin blends contain at least 0.1 wt % of antioxidant, based on the total weight of the composition. In one or more embodiments, the amount of antioxidant(s) can range from about 0.1 wt % to about 5 wt %, based on the total weight of the composition. In one or more embodiments, the amount of antioxidant(s) can range from a low of about 0.1 wt %; 0.2 wt %; or 0.3 wt %; to a high of about 1 wt %; 2.5 wt %; or 5 wt %, based on the total weight of the composition. In one or more embodiments, the amount of antioxidant(s) is about 0.1 wt %, based on the total weight of the composition. In one or more embodiments, the amount of antioxidant(s) is about 0.2 wt %, based on the total weight of the composition. In one or more embodiments, the amount of antioxidant(s) is about 0.3 wt %, based on the total weight of the composition. In one or more embodiments, the amount of antioxidant(s) is about 0.4 wt %, based on the total weight of the composition. In one or more embodiments, the amount of antioxidant(s) is about 0.5 wt %, based on the total weight of the composition.

Blending and Additives

In one or more embodiments, the individual materials and components can be blended by melt-mixing to form a blend. Examples of machinery capable of generating the shear and mixing include extruders with kneaders or mixing elements with one or more mixing tips or flights, extruders with one or more screws, extruders of co or counter rotating type, Banbury mixer, Farrell Continuous mixer, and the Buss Kneader. The type and intensity of mixing, temperature, and residence time required can be achieved by the choice of one of the above machines in combination with the selection of kneading or mixing elements, screw design, and screw speed (<3000 RPM).

In one or more embodiments, the co-agents, antioxidants, and/or other additives can be introduced at the same time as the other resin components or later downstream in case of using an extruder or Buss kneader or only later in time. In addition to the co-agents and antioxidants described, other additives can include antiblocking agents, antistatic agents, ultraviolet stabilizers, foaming agents, and processing aids. The additives can be added to the blend in pure form or in masterbatches.

Cured Products

In a particular embodiment, the crosslinking is accomplished by electron beam or simply "ebeam" after shaping or extruding the composite. Suitable ebeam equipment is available from E-BEAM Services, Inc. In a particular embodiment, electrons are employed at a dosage of about 100 kGy or less in multiple exposures. The source can be any electron beam generator operating in a range of about 150 Key to about 12 mega-electron volts (MeV) with a power output capable of supplying the desired dosage. The electron voltage can be adjusted to appropriate levels which may be, for example, 100,000; 300,000; 1,000,000; 2,000,000; 3,000,000; 6,000,000. A wide range of apparatus for irradiating polymers and polymeric articles is available.

Effective irradiation is generally carried out at a dosage between about 10 kGy to about 350 kGy; preferably from about 20 to about 350 kGy; or from about 30 to about 250 kGy; or from about 40 to about 200 kGy. In a particular aspect of this embodiment, the irradiation is carried out at room temperature.

In another embodiment, crosslinking can be accomplished by exposure to one or more chemical agents in addition to the e-beam cure. Illustrative chemical agents include but are not limited to peroxides and other free radical generating agents, sulfur compounds, phenolic resins, and silicon hydrides. In a particular aspect of this embodiment, the crosslinking agent is either a fluid or is converted to a fluid such that it can be applied uniformly to the composite. Fluid crosslinking agents include those compounds which are gases (e.g., sulfur dichloride), liquids (e.g., Trigonox C, available from Akzo Nobel), solutions (e.g., dicumyl peroxide in acetone, or suspensions thereof (e.g., a suspension or emulsion of dicumyl peroxide in water, or redox systems based on peroxides).)

Illustrative peroxides include, but are not limited to: dicumyl peroxide; di-tert-butyl peroxide; t-butyl perbenzoate; benzoyl peroxide; cumene hydroperoxide; t-butyl peroctoate; methyl ethyl ketone peroxide; 2,5-dimethyl-2,5-di(t-butyl peroxy)hexane; lauryl peroxide; tert-butyl peracetate. When used, peroxide curatives are generally selected from organic peroxides. Examples of organic peroxides include, but are not limited to: di-tert-butyl peroxide; dicumyl peroxide; t-butylcumyl peroxide; α,α-bis(tert-butylperoxy) diisopropyl benzene; 2,5 dimethyl 2,5-di(t-butylperoxy)hexane; 1,1-di(t-butylperoxy)-3,3,5-trimethyl cyclohexane; -butyl-4, 4-bis(tert-butylperoxy) valerate; benzoyl peroxide; lauroyl peroxide; dilauroyl peroxide; 2,5-dimethyl-2,5-di(tert-butylperoxy) hexene-3; and mixtures thereof. Also, diaryl peroxides; ketone peroxides; peroxydicarbonates; peroxyesters; dialkyl peroxides; hydroperoxides; peroxyketals; and mixtures thereof may be used.

In one or more embodiments, the crosslinking can be carried out using hydrosilylation techniques.

In one or more embodiments, the crosslinking can be carried out under an inert or oxygen-limited atmosphere. Suitable atmospheres can be provided by the use of helium, argon, nitrogen, carbon dioxide, xenon and/or a vacuum.

Crosslinking either by chemical agents or by irradiation can be promoted with a crosslinking catalyst, such as organic bases, carboxylic acids, and organometallic compounds including organic titanates and complexes or carboxylates of lead; cobalt; iron; nickel; zinc; and tin (such as dibutyltindilaurate; dioctyltinmaleate; dibutyltindiacetate; dibutyltindioctoate; stannous acetate; stannous octoate; lead naphthenate; zinc caprylate; cobalt naphthenate; and the like).

Articles

The multilayer constructions are particularly useful for applications requiring any one or more of the following properties or attributes: absorbency; liquid repellency; resilience; stretch; softness; strength; flame retardancy; washability; cushioning; filtering; bacterial barrier; and sterility. Illustrative applications and uses can include, but are not limited to, hygiene; medical; filters; and geotextiles, among others.

For example, the multilayer constructions can be used to make baby diapers; feminine hygiene napkins; adult incontinence products; personal hygiene wipes; bandages; wound dressings; air filters; liquid filters; household wipes; shop towels; battery separators; vacuum cleaner bags; cosmetic pads; food packaging; clothing; apparels; medical garments; and disposable underwear. Particularly suitable uses include closure systems on baby diapers; pull-ups; training pants; adult incontinence briefs and diapers; bandages; and other single use or disposable items.

Common filtering uses include gasoline; oil and air filters; water; coffee and tea bags; liquid cartridge and bag filters; vacuum bags; and allergen membranes. Illustrative geotextiles and uses thereof include soil stabilizers and roadway underlayment; foundation stabilizers; erosion control; canals construction; drainage systems; geomembranes protection; frost protection; agriculture mulch; pond and canal water barriers; and sand infiltration barrier for drainage tile.

Additional articles and uses of the multilayer construction provided herein can include, for example, carpet backing; marine sail laminates; table cover laminates; chopped strand mat; backing/stabilizer for machine embroidery; packaging; insulation; pillows; cushions; and upholstery padding; batting in quilts or comforters; consumer and mailing envelopes; tarps; as well as tenting and transportation (lumber, steel) wrapping.

The entire article can be formed from the multiplayer constructions, or the multilayer constructions can form individual sections or portions thereof. For example, in baby diapers, it is envisaged that the multilayer constructions form at least part of the back sheet, wings, and/or tabs.

Provided below are additional numbered embodiments:

1. A method for forming a temperature resistant multilayer composite, comprising:
   extruding one or more polyolefin polymers having a MFR from less than 90 dg/min through at least one die having a plurality of nozzles to form a plurality of continuous fibers, at least one die operating at a melt pressure from greater than 500 psi (3.45 MPa) to form at least one elastic meltblown layer;
   adhering the at least one elastic meltblown layer to at least one extensible layer to form a multilayer composite; and
   at least partially crosslinking the elastic meltblown layer or the extensible layer or both.
2. The method of embodiment 1, wherein the elastic meltblown fabric is adhered to at least one face of a spunlace fabric having a basis weight within the range from 10 to 150 g/m$^2$.
3. The method of embodiments 1 or 2, wherein the extensible fabric comprises from greater than 10 wt %, by weight of the fabric, of a polyolefin.
4. The method according to any claims 1 to 3, further comprising passing the multilayer construction through a hydroentangling apparatus.
5. The method according to any embodiment 1 to 4, wherein the die is operating at a melt temperature from less than 280° C.
6. The method according to any embodiment 1 to 5, wherein the components are melt blended in an apparatus where visbreaking agents are excluded.
7. The method according to any embodiment 1 to 6, wherein the polyolefin polymer is a propylene-α-olefin copolymer having a comonomer-derived content within the range from 5 to 35 wt % by weight of the copolymer.
8. The method according to any embodiment 1 to 7, wherein the construction has a peak force value (ASTM 2261-07a) within the range from 1 and 2 lbs at an Elongation of greater than 1000%.
9. The method according to any embodiment 1 to 8, wherein the number of continuous fibers per square inch of the elastic meltblown fabric is within the range from 20 to 500 fibers/in$^2$.
10. The method according to any embodiment 1 to 9, wherein the elastic meltblown fabric possesses an MD Elongation from less than 100% and a CD Elongation from greater than 100%.
11. The method according to any embodiment 1 to 10, wherein the extensible fabric comprises at least one layer of a spunlace fabric having a basis weight within the range of from 10 to 150 g/m$^2$ and comprising from greater than 10 wt %, by weight of the fabric, of a polyolefin.
12. The method according to any embodiment 1 to 11, wherein the extensible fabric has an Ultimate Elongation from greater than 200%.
13. The method according to any embodiment 1 to 12, wherein the multilayer construction or its individual layers are not mechanically stretched or oriented.
14. The method according to any embodiment 1 to 13, wherein styrenic block copolymers, as a fabric layer or component of a fabric layer, are substantially absent.
15. An absorbent article comprising the multilayer construction according to any claims 1 to 14.
16. The article of embodiment 15, wherein the article is selected from baby diapers, pullups, training pants, adult incontinence briefs and diapers, panty liners, sanitary napkins, medical garments, and bandages.

17. A method for forming a temperature resistant multilayer composite, comprising:
   - extruding one or more elastic or extensible resins through one or more dies having a plurality of nozzles to form a first plurality of continuous fibers;
   - extruding one or more inelastic resins or extensible through one or more dies simultaneously or nearly simultaneously with the one or more elastic resins to form a second plurality of continuous fibers; and
   - crosslinking the extruded resin using electron beam radiation having an e-beam dose of about 200 kGy or less.

18. The method of embodiment 17, wherein the e-beam dose is about 100 kGy.

19. The method of embodiments 17 or 18, wherein the e-beam dose ranges of from 40 kGy to about 60 kGy.

20. An absorbent article comprising the cured multilayer construction according to any embodiment 17 to 19.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for forming a temperature resistant multilayer composite, comprising:
   - extruding a blend of one or more propylene-based elastic resins and a coagent through one or more dies having a plurality of nozzles to form a first plurality of continuous fibers, wherein the first plurality of continuous fibers form a first meltblown layer, where the propylene-based elastic resin is a random copolymer and comprises 80 to 95 wt % propylene and has a heat of fusion less than 75 J/g and a MFR of greater than 50 dg/min, and where the coagent is selected from multifunctional acrylates and methacrylates, functionalized polybutadiene resins, functionalized cyanurate, and allyl isocyanurate;
   - extruding one or more extensible resins through one or more dies simultaneously or nearly simultaneously with the one or more elastic resins to form a second plurality of continuous fibers, wherein the second plurality of continuous fibers form a second layer;
   - wherein the first meltblown layer and the second layer contact each other while the first meltblown layer is still forming, such that the plurality of continuous fibers are still in a melt or partial melt state when contacting the at least one extensible resin, thereby forming a multilayer composite; and
   - exposing the multilayer composite to electron beam radiation having an e-beam dose of about 200 kGy or less, thereby crosslinking the first meltblown layer and the second layer.

2. The method of claim 1, wherein the e-beam dose is about 100 kGy.

3. The method of claim 1, wherein the e-beam dose ranges from 40 kGy to about 60 kGy.

4. The method of claim 1, wherein the second layer comprises greater than 10 wt %, by weight of the layer, of a polyolefin.

5. The method of claim 1, further comprising passing the multilayer composite through a hydroentangling apparatus.

6. The method of claim 1, wherein at least one of the propylene-based elastic resins is a propylene-α-olefin copolymer having a comonomer-derived content within the range from 5 to 35 wt % by weight of the copolymer.

7. The method of claim 1, wherein the multilayer composite or its individual layers are not mechanically stretched or oriented.

* * * * *